(12) United States Patent
Lafanechère et al.

(10) Patent No.: US 12,409,162 B2
(45) Date of Patent: Sep. 9, 2025

(54) CARBAZOLE DERIVATIVES SENSITIZING CELLS TO ANTI-CANCER AGENTS

(71) Applicant: CENTRE NATIONAL DE LA RECHERCHE SCIENTIFIQUE, Paris (FR)

(72) Inventors: Laurence Lafanechère, Grenoble (FR); Renaud Prudent, Renage (FR); Lauralie Peronne, Grenoble (FR); Marc Billaud, Saint Martin d'Heres (FR); Audrey Vernet, Saint Julien du Serre (FR); Eric Denarier, Grenoble (FR); Patrick Dallemagne, Seulline (FR); Sylvain Rault, Moult (FR); Peggy Suzanne, Cairon (FR); Jean-charles Lancelot, Tour en Bessin (FR); Serge Perato, Chatillon (FR); Aurélien Lesnard, Demouville (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 547 days.

(21) Appl. No.: 17/767,744

(22) PCT Filed: Oct. 12, 2020

(86) PCT No.: PCT/EP2020/078585
§ 371 (c)(1),
(2) Date: Apr. 8, 2022

(87) PCT Pub. No.: WO2021/069736
PCT Pub. Date: Apr. 15, 2021

(65) Prior Publication Data
US 2023/0404973 A1   Dec. 21, 2023

(30) Foreign Application Priority Data

Oct. 11, 2019  (EP) ..................................... 19306335
Aug. 19, 2020  (EP) ..................................... 20315388

(51) Int. Cl.
*A61K 31/403*   (2006.01)
*A61K 31/337*   (2006.01)
*A61P 35/00*    (2006.01)
*C07D 403/04*   (2006.01)

(52) U.S. Cl.
CPC .......... *A61K 31/403* (2013.01); *A61K 31/337* (2013.01); *A61P 35/00* (2018.01); *C07D 403/04* (2013.01); *A61L 2300/416* (2013.01)

(58) Field of Classification Search
None
See application file for complete search history.

(56) References Cited

FOREIGN PATENT DOCUMENTS

EP   2 455 378 A1   5/2012

OTHER PUBLICATIONS

Eur. J. Med. Chem. 1998, v.23, p. 119-124.
Lancelot et al., Fleterocyles (1990), 31 (2),.
Lancelot et al., Gazzetta chimica Italiana, 121 , 1991.
Panno et al., Nuovi 1 ,4-Dimethil carbazoli: Sintesi, Reattivitae valutazione Biologica. Tesi Di Dottorato d'Universita Calabria: Universita Della Calabria, 2011.
Tabka et al., European Journal of Medicinal Chemistry (1989), 24(6), 605-610.
Pannala et al.; "Synthesis, Molecular Docking, in vitro Antiproliferative and Antioxidant Activity of Novel Pyrrolidinyl-Carbazole Derivatives"; Current Organic Synthesis, vol. 14, No. 8, Feb. 3, 2018.
(Continued)

*Primary Examiner* — Kortney L. Klinkel
*Assistant Examiner* — Sophia Reilly
(74) *Attorney, Agent, or Firm* — WCF IP

(57) ABSTRACT

The invention concerns a compound of formula (I), Formula (I), wherein R, $R^1$ and $R^2$ are independently selected form the group consisting of: —a hydrogen atom, —a halogen atom, —an alkyl group, linear, cyclic or branched, saturated or unsaturated, possibly substituted, comprising from 1 to 10 carbon atoms, —an acyl group comprising from 1 to 10 carbon atoms, —a carboxyl group, —an amido group comprising from 1 to 10 carbon atoms, and —an imino group, possibly substituted by an alkyl group, linear, cyclic or branched, saturated or unsaturated, and wherein $R^3$, $R^4$, $R^5$ and $R^6$ are independently selected form the group consisting of: —a hydrogen atom, —a halogen atom, —a hydroxyl group, —an alkyl group, linear, cyclic or branched, saturated or unsaturated, possibly substituted, comprising from 1 to 10 carbon atoms, —an alkoxy group comprising from 1 to 10 carbon atoms, —an acyl group comprising from 1 to 10 carbon atoms, —a carbonate group from 1 to 10 carbon atoms, —a carboxyl group, and —a cyano group.

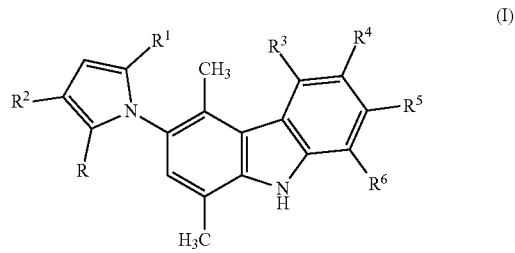

15 Claims, 9 Drawing Sheets

(56) References Cited

OTHER PUBLICATIONS

Perche et al.; "Synthesis and formylation of 3-(2,5-dimethyl-1-pyrrolyl)-9-ethylcarbazole"; Bulletin de la Societe Chimique de France, Jan. 1, 1974, pp. 1117-1118.

CARBAZOLE DERIVATIVES SENSITIZING CELLS TO ANTI-CANCER AGENTS

The present invention concerns new carbazole derivatives of formula (I).

The present invention also concerns a method of preparation of compounds of formula (I).

The present invention also concerns pharmaceutical compositions comprising such compounds of formula (I).

Finally, the present invention also concerns compounds of formula (I) for use in a method of treatment of a cancer.

STATE OF THE ART

Currently, a variety of cancers including lung, breast and ovarian cancers are treated using paclitaxel. Paclitaxel is an agent that targets cell microtubules, binding to the taxane-site of β-tubulin and stabilizing microtubule lattice by strengthening lateral and/or longitudinal tubulin contacts in microtubules. At high concentrations, it promotes microtubule assembly. At low and clinically relevant concentrations, paclitaxel primarily suppresses microtubule dynamics without significantly affecting the microtubule-polymer mass.

However, the low solubility of paclitaxel, its toxicity and its susceptibility to multiple drug resistance mechanisms still impose serious limits on its use.

In addition, germinal mutations of LKB1 gene, known as a tumor suppressor gene, are frequently observed in cases of lung adenocarcinoma or uterine tumors. Such mutations are also responsible for the large majority of Peutz-Jeghers syndrome cases, this syndrome inducing the formation of polyps and an increased incidence of malignant tumors, specifically digestive and breast tumors.

This high prevalence of LKB1-deficient cells in these cancers shows the urgency to focus on the development of treatments targeting such cells.

AIMS OF THE INVENTION

One aim of the present invention is to provide improved treatments against cancers that could alleviate the above limitations.

In particular, the present invention aims to provide a solution to the technical problem of reducing the toxicity of compounds stabilizing cell microtubules, and in particular of paclitaxel.

The present invention aims to provide a solution to the technical problem of reducing the resistance to compounds stabilizing the microtubules, in particular of the resistance to paclitaxel.

The present invention aims to provide a solution to the technical problem of providing new treatments targeting LKB1-deficient cells.

One aim of the present invention is to provide compounds for use in a pharmaceutical treatment, notably against a cancer, that could alleviate the above technical limitations.

Another aim of the present invention is to reduce the resistance to compounds stabilizing the microtubules, in particular the resistance to paclitaxel.

Another aim of the present invention is to provide compounds being selectively cytotoxic against LKB1-deficient cells.

DETAILED DESCRIPTION OF THE INVENTION

The present invention concerns a compound of formula (I)

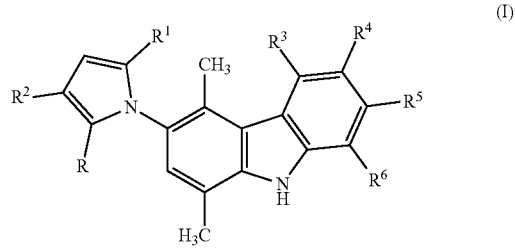

wherein R, $R^1$ and $R^2$ are independently selected form the group consisting of:
- a hydrogen atom,
- a halogen atom,
- an alkyl group, linear, cyclic or branched, saturated or unsaturated, possibly substituted, comprising from 1 to 10 carbon atoms,
- an acyl group comprising from 1 to 10 carbon atoms,
- a carboxyl group,
- an amido group comprising from 1 to 10 carbon atoms, and
- an imino group, possibly substituted by an alkyl group, linear, cyclic or branched, saturated or unsaturated, and wherein $R^3$, $R^4$, $R^5$ and $R^6$ are independently selected form the group consisting of:
- a hydrogen atom,
- a halogen atom,
- a hydroxyl group,
- an alkyl group, linear, cyclic or branched, saturated or unsaturated, possibly substituted, comprising from 1 to 10 carbon atoms,
- an alkoxy group comprising from 1 to 10 carbon atoms,
- an acyl group comprising from 1 to 10 carbon atoms,
- a carbonate group from 1 to 10 carbon atoms,
- a carboxyl group, and
- a cyano group.

The compound of formula (I) of the invention may also be in the form of its tautomeric, racemic, enantiomeric or polymorphic forms or pharmaceutically-acceptable salts.

Surprisingly, it was discovered by present inventors that a compound of formula (I) of the invention potentiates the effect of a compound stabilizing cell microtubules, in particular the effect of paclitaxel, without significantly increasing its toxicity. Such a compound of formula (I) could allow the use in cancer therapy of lower doses of a compound stabilizing microtubules, in particular of paclitaxel, and may limit the occurrence of resistances.

Compounds of formula (I) are able to sensitize cells to a low, non-toxic dose of a compound stabilizing the microtubules, in particular of paclitaxel.

Compounds of formula (I) alone have no major effect on interphase microtubule dynamics and show moderate cytotoxicity. However, compounds of formula (I) exert synergistic cytotoxic effects with compounds stabilizing the microtubules, in particular with paclitaxel.

Without being bound by theory, the inventors consider that compounds of formula (I) induce a modulation of microtubule dynamics that increases the accumulation of compounds stabilizing the microtubules inside the microtubules.

It was also surprisingly discovered by the present inventors that compounds of formula (I) of the invention are selectively cytotoxic against LKB1-deficient cells.

The invention refers to a "substituted" group or moiety, which is known to mean that at least one hydrogen radical of said group or moiety is replaced with an atom or a group of atoms called substituent.

Examples of preferred substituents are halogen (chloro-, iodo-, bromo-, or fluoro-); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups.

The invention refers to an "acyl" group, which is known as a moiety derived by the removal of the hydroxyl group from a carboxylic acid. Examples of acyl groups are aldehydes, ketones, esters, amides or acyl chlorides.

Preferably, in the compound of formula (I) according to the invention, R, $R^1$ and $R^2$ are independently selected from the group consisting of:
  a hydrogen atom,
  a halogen atom,
  an alkyl group of formula —$C_nH_{2n+1-x}X_x$, X being selected from the group consisting of a hydrogen atom, a halogen atom, a hydroxyl group, and n being an integer between 1 and 10 and x being the number of X present in the alkyl group, and preferably x being 1 and X being in terminal position in the alkyl group,
  an acyl group of formula —$C(O)OR_a$, $R_a$ being a linear and saturated alkyl group comprising from 1 to 9 carbon atoms,
  an acyl group of formula —C(O)H,
  a carboxyl group (—COOH),
  an amido group of formula —$C(O)NR_b$, $R_b$ being a linear and saturated alkyl group comprising from 1 to 9 carbon atoms, and
  an imino group of formula —C=N—$R_c$, $R_c$ being selected from the group consisting of a hydrogen atom or an alkyl group, linear, saturated and comprising from 1 to 10 carbon atoms, or a phenyl group, and
$R^3$, $R^4$, $R^5$ and $R^6$ are independently selected from the group consisting of:
  a hydrogen atom,
  a halogen atom,
  a hydroxyl group,
  an alkyl group of formula —$C_nH_{2+1}$, linear, saturated and n being an integer between 1 and 10,
  an alkoxy group of formula —$OR_d$, $R_d$ being a linear and saturated alkyl group comprising from 1 to 9 carbon atoms,
  an acyl group of formula —$C(O)OR_a$, $R_a$ being a linear and saturated alkyl group comprising from 1 to 9 carbon atoms,
  an acyl group of formula —$C(O)R_e$, $R_e$ being a hydrogen atom or an alkyl group, linear, cyclic or branched, saturated or unsaturated, possibly substituted, comprising from 1 to 10 carbon atoms,
  a carbonate group of formula —$OC(O)OR_f$, $R_f$ being a linear and saturated alkyl group comprising from 1 to 9 carbon atoms,
  a carboxyl group (—COOH), and
  a cyano group (—CN).

More preferably, in the compound of formula (I) according to the invention, R and $R^1$ are independently selected from the group consisting of:
  a hydrogen atom,
  a halogen atom,
  an alkyl group, linear, saturated and comprising from 1 to 10 carbon atoms,
$R^2$ is selected from the group consisting of:
  a hydrogen atom,
  a halogen atom,
  an alkyl group of formula —$C_nH_{2n+1-x}X_x$, X being selected from the group consisting of a hydrogen atom, a halogen atom, a hydroxyl group, and n being an integer between 1 and 10 and x being the number of X present in the alkyl group, and preferably x being 1 and X being in terminal position in the alkyl group,
  an acyl group of formula —$C(O)OR_a$, $R_a$ being a linear and saturated alkyl group comprising from 1 to 9 carbon atoms,
  an acyl group of formula —C(O)H,
  a carboxyl group (—COOH),
  an amido group of formula —$C(O)NR_b$, $R_b$ being a linear and saturated alkyl group comprising from 1 to 9 carbon atoms, and
  an imino group of formula —C=N—$R_c$, $R_c$ being selected from the group consisting of a hydrogen atom or an alkyl group, linear, saturated and comprising from 1 to 10 carbon atoms, or a phenyl group,
$R^3$, $R^5$ and $R^6$ are independently selected from the group consisting of:
  a hydrogen atom,
  a halogen atom,
  an alkyl group of formula —$C_nH_{2n+1}$, linear, saturated and n being an integer between 1 and 10, and
$R^4$ is selected from the group consisting of:
  a hydrogen atom,
  a halogen atom,
  a hydroxyl group,
  an alkyl group of formula —$C_nH_{2n+1}$, linear, saturated and n being an integer between 1 and 10,
  an alkoxy group of formula —$OR_d$, $R_d$ being a linear and saturated alkyl group comprising from 1 to 9 carbon atoms,
  an acyl group of formula —$C(O)OR_a$, $R_a$ being a linear and saturated alkyl group comprising from 1 to 9 carbon atoms,
  an acyl group of formula —$C(O)R_e$, $R_e$ being a hydrogen atom or an alkyl group, linear, cyclic or branched, saturated or unsaturated, possibly substituted, comprising from 1 to 10 carbon atoms, a carbonate group of formula —OC(O)OR$_f$, R$_f$ being a linear and saturated alkyl group comprising from 1 to 9 carbon atoms, a carboxyl group (—COOH), and a cyano group (—CN).

Even more preferably, in the compound of formula (I) according to the invention, R and R$^1$ are independently selected from the group consisting of a hydrogen atom, a chloride atom and a methyl group, R$^2$ is selected from the group consisting of a hydrogen atom, a methyl group, a —COH group, an alkyl group of formula —CH$_2$X, X being selected from the group consisting of a chloride atom, a bromide atom, a iodine atom and a hydroxyl group, an acyl group of formula —C(O)OR$_a$, R$_a$ being a methyl group or an ethyl group, an acyl group of formula —C(O)H, a carboxyl group (—COOH), an amido group of formula —C(O)NR$_b$, R$_b$ being a methyl group or an ethyl group, and an imino group of formula —C=N—R$_c$, R$_c$ being a phenyl group, R$^3$, R$^5$ and R$^6$ are independently selected from the group consisting of a hydrogen atom, a chloride atom, a methyl group and an ethyl group, and R$^4$ is selected from the group consisting of a hydrogen atom, a methyl group, a hydroxyle group, a chloride atom, a bromide atom, a fluoride atom, a iodine atom, an alkoxy group of formula —OR$_d$, R$_d$ being a methyl group or an ethyl group, an acyl group of formula —C(O)OR$_a$, R$_a$ being a methyl group or an ethyl group, an acyl group of formula —C(O)R$_e$, R$_e$ being a methyl group, an ethyl group, a linear propyl group, a linear pentyl group, —CH$_2$CH$_2$-cyclopentyl group and a (para-methyl)phenyl group, a carbonate group of formula —OC(O)OR$_f$, R$_f$ being a methyl group or an ethyl group, a carboxyl group (—COOH), and a cyano group (—CN).

Advantageously, in the compound of formula (I) according to the invention, R and R$^1$ are independently selected from the group consisting of a hydrogen atom and a methyl group, R$^2$ is selected from the group consisting of a hydrogen atom, a —COH group and a —CH$_2$OH group, R$^3$, R$^5$ and R$^6$ are independently selected from the group consisting of a hydrogen atom, a chloride atom and an ethyl group, and R$^4$ is selected from the group consisting of a hydrogen atom, a hydroxyle group, a chloride atom, a bromide atom, a fluoride atom, a carbonate group of formula —OC(O)OR$_f$, R$_f$ being an ethyl group and an acyl group of formula —C(O)OR$_a$, R$_a$ being a methyl group.

According to an embodiment, the compound of formula (I) according to the invention is characterized in that at least three of the substituents selected from the group consisting of R$^3$, R$^4$, R$^5$ and R$^6$ are a hydrogen atom.

According to an embodiment, in the compound of formula (I) R$^4$ is not a hydrogen atom.

According to an embodiment, in the compound of formula (I) R$^4$ is a halogen atom.

According to an embodiment, the compound of formula (I) comprises at least one of the substituents selected from the group consisting of R, R$^1$ and R$^2$ is a hydrogen atom.

According to an embodiment, the compound of formula (I) comprises at least two of the substituents selected from the group consisting of R, R$^1$ and R$^2$ are a hydrogen atom.

According to an embodiment, R=R$^1$=R$^2$=H.

In a preferred embodiment, the compound of formula (I) is selected from the group consisting of

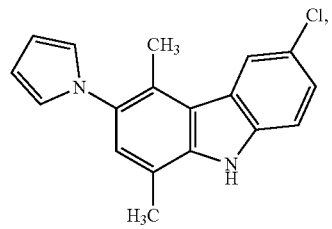

(I-a)

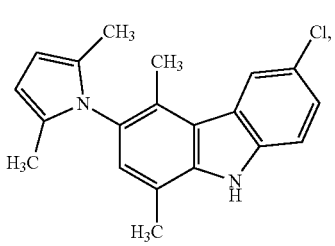

(I-b)

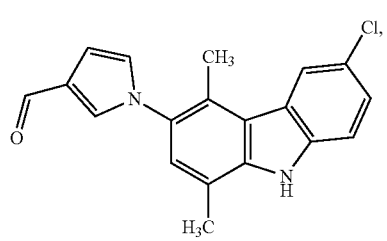

(I-c)

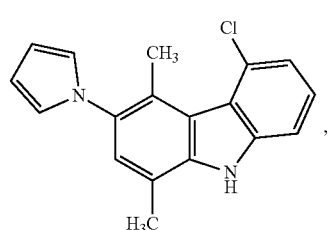

(I-d)

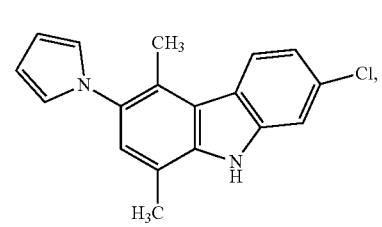

(I-e)

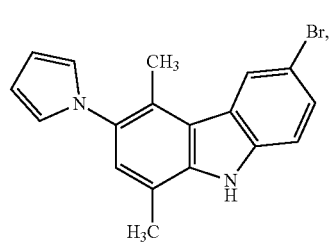

(I-f)

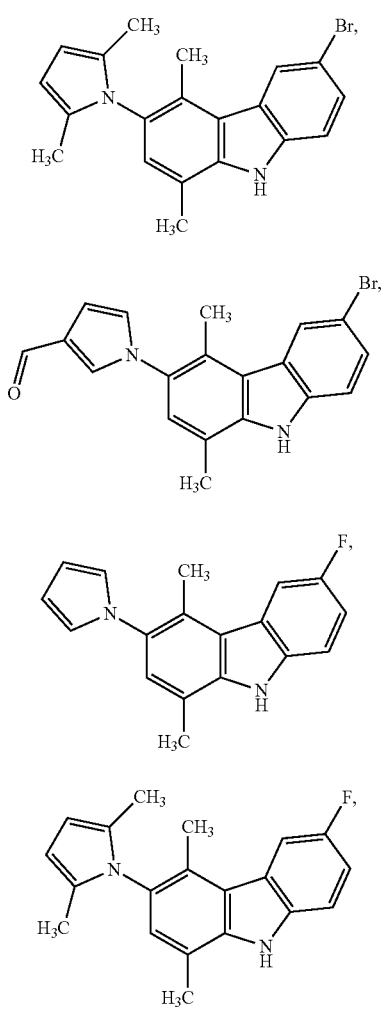
(I-g)
(I-h)
(I-i)
(I-j)
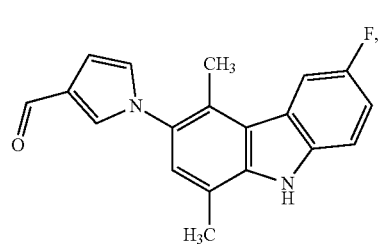
(I-k)
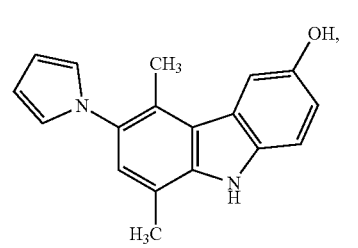
(I-m)
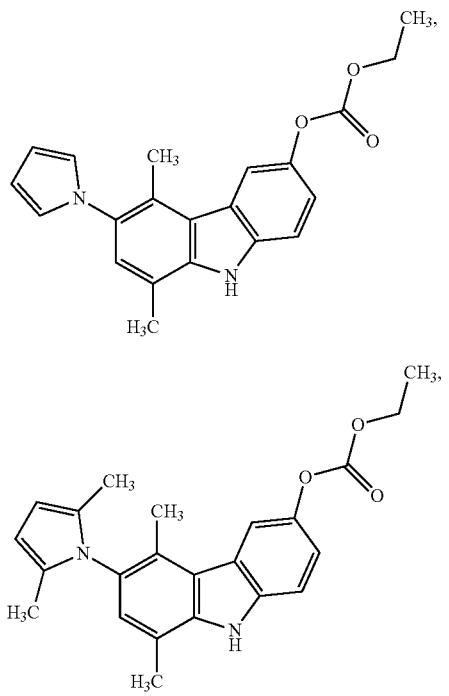
(I-n)
(I-o)
(I-p)
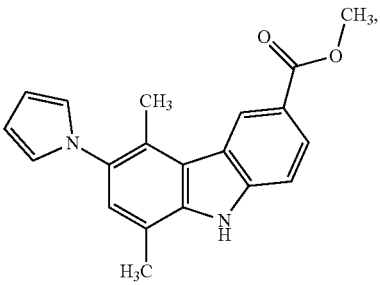
(I-q) and
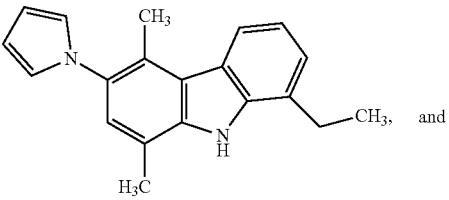
(I-s)

In a preferred embodiment, the compound of formula (I) is selected from the group consisting of
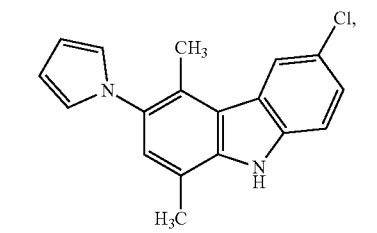
(I-a)
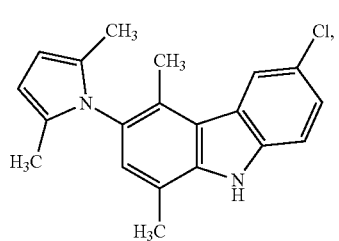
(I-b)
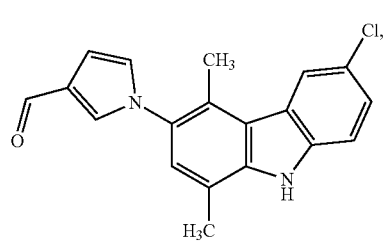
(I-c)
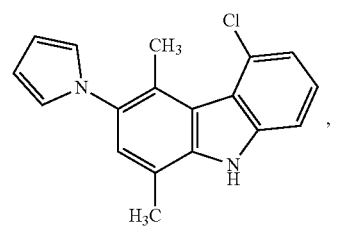
(I-d)
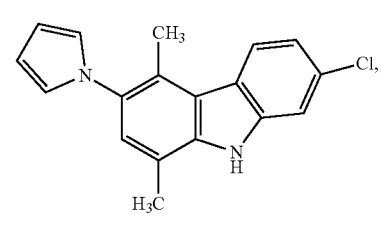
(I-e)
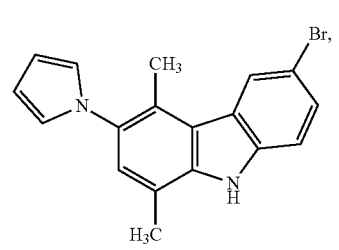
(I-f)
-continued
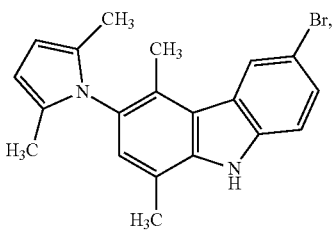
(I-g)
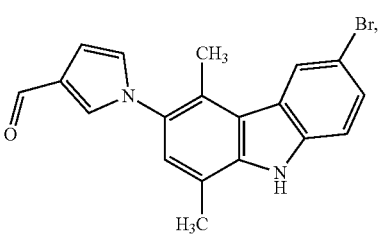
(I-h)
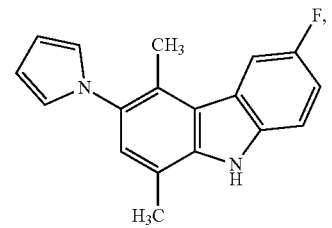
(I-i)
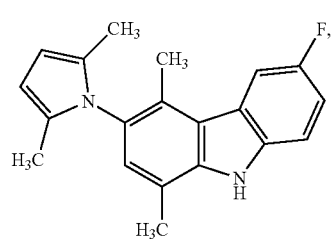
(I-j)
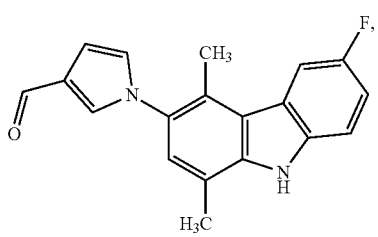
(I-k)
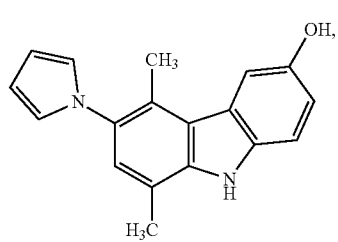
(I-m)

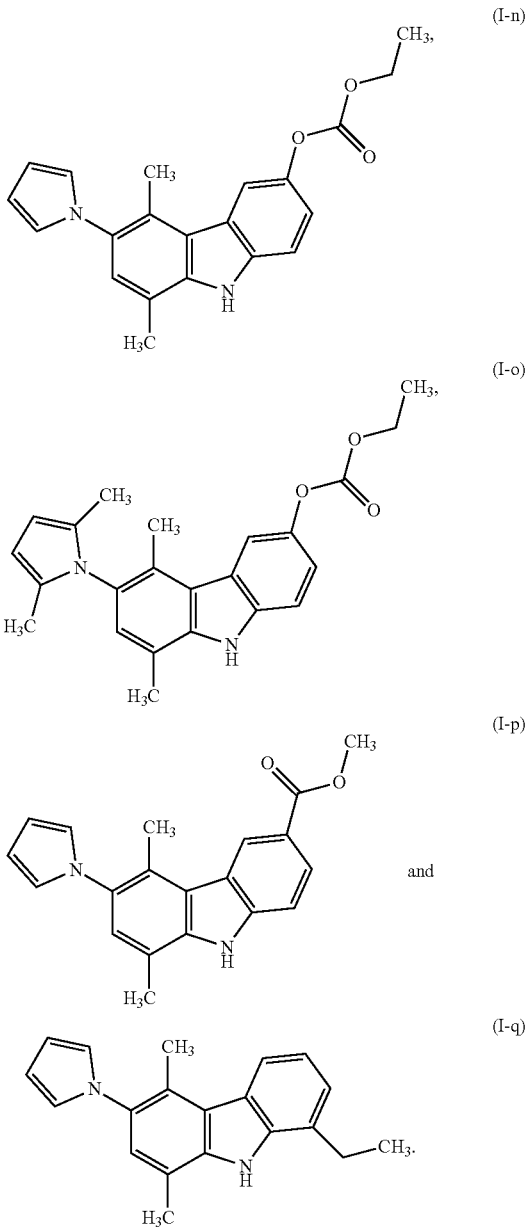

More preferably, a compound of formula (I) is selected from the group consisting of a compound of formula (I-a), a compound of formula (I-c), a compound of formula (I-s), and any combination thereof.

Advantageously, the compound of formula (I) is a compound of formula (I-a).

Advantageously, the compound of formula (I) is a compound of formula (I-c), a compound of formula (I-s), and any combination thereof.

The present invention also concerns a method of preparation of a compound of formula (I) according to the invention, comprising the step a) of contacting a compound of formula (II)

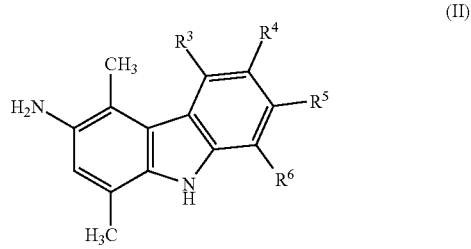

with a compound of formula (III)

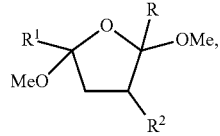

or a compound of formula (IV)

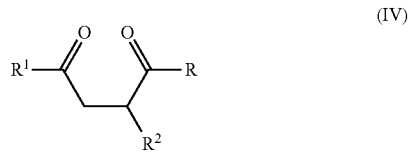

Preferably, a compound of formula (I) is selected from the group consisting of a compound of formula (I-a), a compound of formula (I-f), a compound of formula (I-h), a compound of formula (I-e), a compound of formula (I-m), a compound of formula (I-n), a compound of formula (I-c), a compound of formula (I-s) and any combination thereof Preferably, a compound of formula (I) is selected from the group consisting of a compound of formula (I-a), a compound of formula (I-f), a compound of formula (I-h), a compound of formula (I-e) and any combination thereof.

Preferably, a compound of formula (I) is selected from the group consisting of a compound of formula (I-a), a compound of formula (I-f), a compound of formula (I-h), and any combination thereof.

Preferably, a compound of formula (I) is selected from the group consisting of a compound of formula (I-a), a compound of formula (I-f), a compound of formula (I-h), a compound of formula (I-c), a compound of formula (I-s), and any combination thereof.

in the presence of an acid, preferably of an organic acid, wherein R, $R^1$ and $R^2$ are independently selected from the group consisting of:
a hydrogen atom,
a halogen atom,
an alkyl group, linear, cyclic or branched, saturated or unsaturated, possibly substituted, comprising from 1 to 10 carbon atoms,
an acyl group comprising from 1 to 10 carbon atoms,
a carboxyl group,
an amido group comprising from 1 to 10 carbon atoms, and
an imino group, possibly substituted by an alkyl group, linear, cyclic or branched, saturated or unsaturated, and
wherein $R^3$, $R^4$, $R^5$ and $R^6$ are independently selected from the group consisting of:
a hydrogen atom,
a halogen atom,
a hydroxyl group, an alkyl group, linear, cyclic or branched, saturated or unsaturated, possibly substituted, comprising from 1 to 10 carbon atoms,
an alkoxy group comprising from 1 to 10 carbon atoms,
an acyl group comprising from 1 to 10 carbon atoms,
a carbonate group comprising from 1 to 10 carbon atoms,
a carboxyl group, and
a cyano group.

Preferably, the method of preparation of a compound of formula (I) according to the invention comprises the step a) of contacting a compound of formula (II)

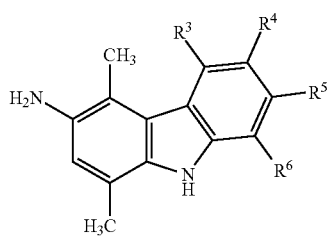

(II)

with a compound of formula (III)

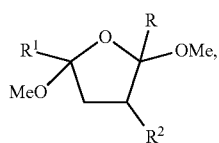

(III)

in the presence of an acid, preferably of an organic acid, wherein R, $R^1$ and $R^2$ are independently selected from the group consisting of:
a hydrogen atom,
a halogen atom,
an alkyl group, linear, cyclic or branched, saturated or unsaturated, possibly substituted, comprising from 1 to 10 carbon atoms,
an acyl group comprising from 1 to 10 carbon atoms,
a carboxyl group,
an amido group comprising from 1 to 10 carbon atoms, and
an imino group, possibly substituted by an alkyl group, linear, cyclic or branched, saturated or unsaturated, and
wherein $R^3$, $R^4$, $R^5$ and $R^6$ are independently selected from the group consisting of:
a hydrogen atom,
a halogen atom,
a hydroxyl group,
an alkyl group, linear, cyclic or branched, saturated or unsaturated, possibly substituted, comprising from 1 to 10 carbon atoms,
an alkoxy group comprising from 1 to 10 carbon atoms,
an acyl group comprising from 1 to 10 carbon atoms,
a carbonate group comprising from 1 to 10 carbon atoms,
a carboxyl group, and
a cyano group.

In one embodiment, the method of preparation of a compound of formula (I), comprises a step a') of placing the compound of formula (III) in contact with said acid, prior to contacting said compound of formula (III) with a compound of formula (II) or (IV), preferably with a compound of formula (II).

Preferably, the acid of the step a) or a') is acetic acid.

Preferably, step a) is carried out at a temperature from 25° C. to 120° C., more preferably from 60° C. to 100° C., typically during a period from 15 minutes to 180 minutes, more preferably from 60 minutes to 150 minutes.

Preferably, step a') is carried out at a temperature from 15° C. to 40° C., more preferably from 20° C. to 30° C., typically during a period from 1 minute to 60 minutes, more preferably from 10 minutes to 20 minutes.

According to a specific embodiment, step a) is carried out in an organic solvent, preferably in an alcohol comprising from 1 to 8 carbon atoms, more preferably in ethanol.

Preferably, in the method of the invention:
R, $R^1$ and $R^2$ are independently selected from the group consisting of:
a hydrogen atom,
a halogen atom,
an alkyl group of formula $-C_nH_{2n+1-x}X_x$, X being selected from the group consisting of a hydrogen atom, a halogen atom, a hydroxyl group, and n being an integer between 1 and 10 and x being the number of X present in the alkyl group, and preferably x being 1 and X being in terminal position in the alkyl group,
an acyl group of formula $-C(O)OR_a$, $R_a$ being a linear and saturated alkyl group comprising from 1 to 9 carbon atoms,
an acyl group of formula $-C(O)H$,
a carboxyl group ($-COOH$),
an amido group of formula $-C(O)NR_b$, $R_b$ being a linear and saturated alkyl group comprising from 1 to 9 carbon atoms, and
an imino group of formula $-C=N-R_c$, $R_c$ being selected from the group consisting of a hydrogen atom or an alkyl group, linear, saturated and comprising from 1 to 10 carbon atoms, or a phenyl group, and
$R^3$, $R^4$, $R^5$ and $R^6$ are independently selected from the group consisting of:
a hydrogen atom,
a halogen atom,
a hydroxyl group,
an alkyl group of formula $-C_nH_{2n+1}$, linear, saturated and n being an integer between 1 and 10,
an alkoxy group of formula $-OR_d$, $R_d$ being a linear and saturated alkyl group comprising from 1 to 9 carbon atoms,
an acyl group of formula $-C(O)OR_a$, $R_a$ being a linear and saturated alkyl group comprising from 1 to 9 carbon atoms,
an acyl group of formula $-C(O)R_e$, $R_e$ being a hydrogen atom or an alkyl group, linear, cyclic or branched, saturated or unsaturated, possibly substituted, comprising from 1 to 10 carbon atoms,
a carbonate group of formula $-OC(O)OR_f$, $R_f$ being a linear and saturated alkyl group comprising from 1 to 9 carbon atoms,
a carboxyl group ($-COOH$), and
a cyano group ($-CN$).

More preferably, in the method of the invention:
R and $R^1$ are independently selected from the group consisting of:
a hydrogen atom,
a halogen atom, an alkyl group, linear, saturated and comprising from 1 to 10 carbon atoms, $R^2$ is selected from the group consisting of:
  a hydrogen atom,
  a halogen atom,
  an alkyl group of formula —$CH_nX$, X being selected from the group consisting of a hydrogen atom, a halogen atom, a hydroxyl group, and n being an integer between 1 and
  an acyl group of formula —$C(O)OR_a$, $R_a$ being a linear and saturated alkyl group comprising from 1 to 9 carbon atoms,
  an acyl group of formula —$C(O)H$,
  a carboxyl group (—COOH),
  an amido group of formula —$C(O)NR_b$, $R_b$ being a linear and saturated alkyl group comprising from 1 to 9 carbon atoms, and
  an imino group of formula —C=N—$R_c$, $R_c$ being selected from the group consisting of a hydrogen atom or an alkyl group, linear, saturated and comprising from 1 to 10 carbon atoms, or a phenyl group, $R^3$, $R^5$ and $R^6$ are independently selected from the group consisting of:
  a hydrogen atom,
  a halogen atom,
  an alkyl group, linear, saturated and comprising from 1 to 10 carbon atoms, and $R^4$ is selected from the group consisting of:
  a hydrogen atom,
  a halogen atom,
  a hydroxyl group,
  an alkyl group, linear, saturated and comprising from 1 to 10 carbon atoms,
  an alkoxy group of formula —$OR_d$, $R_d$ being a linear and saturated alkyl group comprising from 1 to 9 carbon atoms,
  an acyl group of formula —$C(O)OR_a$, $R_a$ being a linear and saturated alkyl group comprising from 1 to 9 carbon atoms,
  an acyl group of formula —$C(O)R_e$, $R_e$ being a hydrogen atom or an alkyl group, linear, cyclic or branched, saturated or unsaturated, possibly substituted, comprising from 1 to 10 carbon atoms,
  a carbonate group of formula —$OC(O)OR_f$, $R_f$ being a linear and saturated alkyl group comprising from 1 to 9 carbon atoms,
  a carboxyl group (—COOH), and
  a cyano group (—CN).

Even more preferably, in the method of the invention:
R and $R^1$ are independently selected from the group consisting of a hydrogen atom, a chloride atom and a methyl group, $R^2$ is selected from the group consisting of a hydrogen atom, a methyl group, a —COH group, an alkyl group of formula —$CH_2X$, X being selected from the group consisting of a chloride atom, a bromide atom, a iodine atom and a hydroxyl group, an acyl group of formula —$C(O)OR_a$, $R_a$ being a methyl group or an ethyl group, an acyl group of formula —$C(O)H$, a carboxyl group (—COOH), an amido group of formula —$C(O)NR_b$, $R_b$ being a methyl group or an ethyl group, and an imino group of formula —C=N—$R_c$, $R_c$ being a phenyl group, $R^3$, $R^5$ and $R^6$ are independently selected from the group consisting of a hydrogen atom, a chloride atom, a methyl group and an ethyl group, and $R^4$ is selected from the group consisting of a hydrogen atom, a methyl group, a hydroxyle group, a chloride atom, a bromide atom, a fluoride atom, a iodine atom, an alkoxy group of formula —$OR_d$, $R_d$ being a methyl group or an ethyl group, an acyl group of formula —$C(O)OR_a$, $R_a$ being a methyl group or an ethyl group, an acyl group of formula —$C(O)R_e$, $R_e$ being a methyl group, an ethyl group, a linear propyl group, a linear pentyl group, —$CH_2CH_2$-cyclopentyl group and a (para-methyl)phenyl group, a carbonate group of formula —$OC(O)OR_f$, $R_f$ being a methyl group or an ethyl group, a carboxyl group (—COOH), and a cyano group (—CN).

Advantageously, in the method of the invention:
R and $R^1$ are independently selected from the group consisting of a hydrogen atom and a methyl group, $R^2$ is selected from the group consisting of a hydrogen atom, a —COH group and —$CH_2OH$ group, $R^3$, $R^5$ and $R^6$ are independently selected from the group consisting of a hydrogen atom, a chloride atom and an ethyl group, and $R^4$ is selected from the group consisting of a hydrogen atom, a hydroxyle group, a chloride atom, a bromide atom, a fluoride atom and a carbonate group of formula —$OC(O)OR_f$, $R_f$ being an ethyl group and an acyl group of formula —$C(O)OR_a$, $R_a$ being a methyl group.

According to an embodiment, in a compound of formula (II) at least three of the substituents selected from the group consisting of $R^3$, $R^4$, $R^5$ and $R^6$ are a hydrogen atom.

According to an embodiment, in a compound of formula (III) at least one of the substituents selected from the group consisting of R, $R^1$ and $R^2$ is a hydrogen atom.

According to an embodiment, in a compound of formula (III) at least two of the substituents selected from the group consisting of R, $R^1$ and $R^2$ are a hydrogen atom.

According to an embodiment, in a compound of formula (III) R=$R^1$=$R^2$=H.

According to an embodiment, in a compound of formula (IV) at least one of the substituents selected from the group consisting of R, $R^1$ and $R^2$ is a hydrogen atom.

According to an embodiment, in a compound of formula (IV) at least two of the substituents selected from the group consisting of R, $R^1$ and $R^2$ are a hydrogen atom.

According to an embodiment, in a compound of formula (IV) R=$R^1$=$R^2$=H.

In a preferred embodiment, in the method according to the invention, compound of formula (II) is selected from the group consisting of

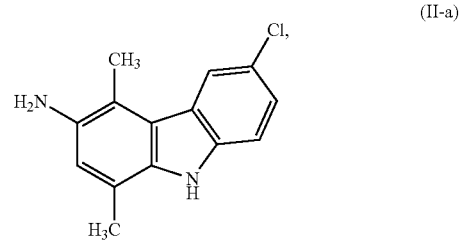

(II-a)

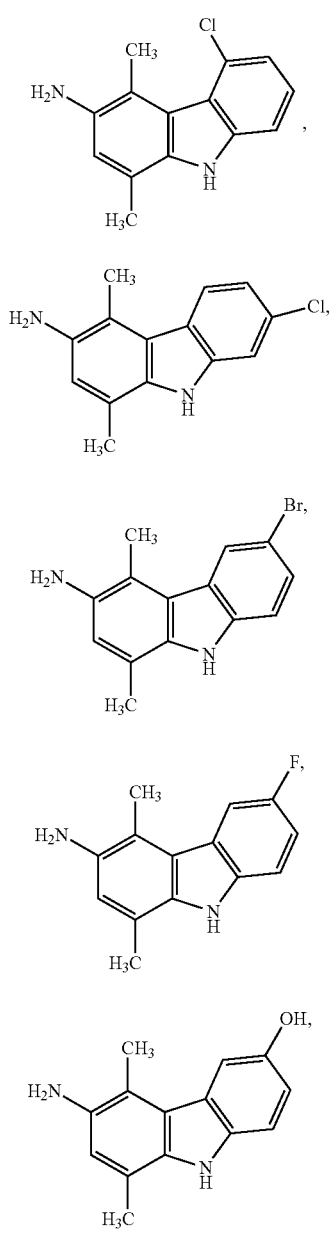

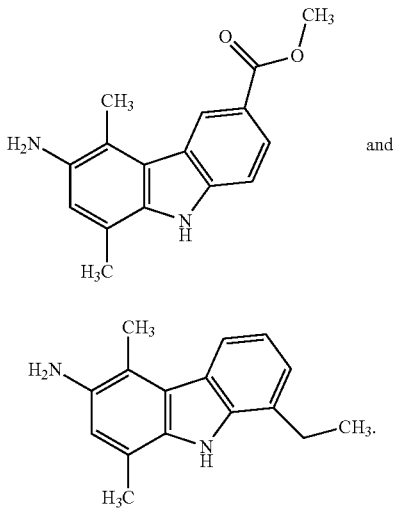

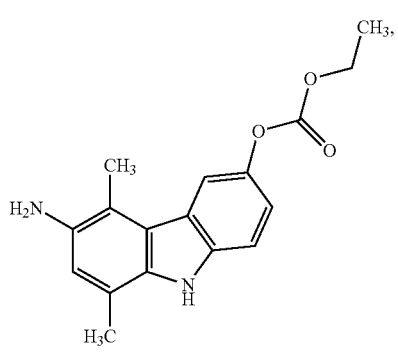

Preferably, a compound of formula (II) is selected from the group consisting of a compound of formula (II-a), a compound of formula (II-c), a compound of formula (II-d), and any combination thereof.

Advantageously, the compound of formula (II) is a compound of formula (II-a).

In another preferred embodiment, compound of formula (III) is selected from the group consisting of

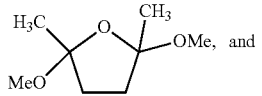

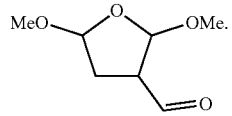

Preferably, the compound of formula (III) is the compound of formula (III-a) or the compound of formula (III-c). Very preferably, the compound of formula (III) is the compound of formula (III-a).

In another preferred embodiment, compound of formula (IV) is selected from the group consisting of

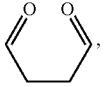

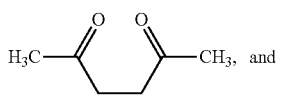

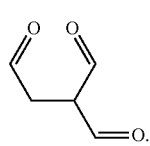
(IV-c)

Preferably the compound of formula (IV) is the compound of formula (IV-b).

According to an embodiment, the method according to the invention further comprises a step b) of chemical modification of the compound obtained from step a). Preferably, step b) is a reduction of an acyl group. Preferably, step b) comprises contacting the compound obtained from step a) with a compound reducing an aldehyde, for example a borohydride salt, preferably with sodium borohydride. More preferably, step b) is the reduction of an aldehyde, preferably by contacting the compound obtained from step a) with a compound reducing an aldehyde, for example a borohydride salt, preferably with sodium borohydride.

Preferably, step b) is carried out at a temperature from 15° C. to 40° C., more preferably from 20° C. to 30° C. typically during a period from 60 minutes to 150 minutes.

The present invention also concerns a pharmaceutical composition, characterized in that it comprises at least one compound of formula (I) according to the invention and at least one pharmaceutically-acceptable excipient.

The expression "pharmaceutically-acceptable excipient" refers to any diluents, adjuvants or vehicles, such as preserving agents, fillers, disintegrating agents, wetting agents, emulsifying agents, suspending agents, solvents, dispersion media, coatings, antibacterial and antifungal agents, isotonic and absorption delaying agents and the like.

The pharmaceutical composition of the present invention may be administered by any suitable route, for example, by oral, buccal, inhalation, sublingual, nasal, percutaneous, i.e. transdermal or parenteral (including intravenous, intramuscular, subcutaneous and intracoronary) administration. Therefore, the pharmaceutical composition of the invention can be provided in various forms, such as in the form of hard gelatin capsules, of capsules, of compressed tablets, of suspensions to be taken orally, of lozenges or of injectable solutions, ointments, or in any other form appropriate to the method of administration.

The exact formulation, route of administration, and dosage can be chosen by the individual physician in view of the patient's conditions. Dosage amount and interval of administration can be adjusted individually to provide plasma levels of compound of formula (I) which are sufficient to maintain the preventive or therapeutic effects. The amount of pharmaceutical composition administered therefore depends on the subject being treated, on the subject's weight, the severity of the affliction and the manner of administration. In one embodiment, the amount of compound of formula (I) administered depends on the response of the subject being treated to the co-administered compound stabilizing microtubules of a cell.

The present invention also concerns a pharmaceutical composition, characterized in that it comprises at least one compound of formula (I) according to the invention, at least one compound stabilizing cell microtubules, preferably a human cell, and at least one pharmaceutically-acceptable excipient.

According to the present invention, a compound stabilizing cell microtubules stabilizes the microtubule polymer and protects from its depolymerization, thus inhibiting the process of cell division as well as other different processes dependent of microtubules dynamics.

Preferably, the compound stabilizing cell microtubules is selected from the group consisting of taxanes, epothilones, TPI-287, carbazitaxel, zampanolide, dactylolide, discodermolide, taccalonolide, davunetide, eleutherobin, dictyostatin and sarcodictyins A and B.

More preferably, the compound stabilizing cell microtubules is selected from the group consisting of taxanes.

Advantageously, the compound stabilizing cell microtubules is paclitaxel.

In particular, the compound stabilizing cell microtubules according to the invention is active in vitro on HeLa cells. According to an embodiment, compound stabilizing cell microtubules according to the invention is active in vitro on HeLa cells at a concentration less than or equal to 5 nM, preferably strictly less than 5 nM.

The present invention also concerns a compound of formula (I) according to the invention, for use in a method of treatment of a disease and/or a disorder selected from the group consisting of a cancer and a disorder involving a deregulation of microtubules.

The present invention also concerns a method of treatment of a disease and/or a disorder selected from the group consisting of a cancer and a disorder involving a deregulation of microtubules, said method comprising the administration of an therapeutically effective of compound of formula (I) to a subject in need thereof.

The present invention also concerns the use of a compound of formula (I) according to the invention for preparing a medicament for treating a disease and/or a disorder selected from the group consisting of a cancer and a disorder involving a deregulation of microtubules.

According to the present invention, a disorder involving a deregulation of microtubules is a disorder involving a deregulated microtubule dynamics.

Preferably, disorder involving a deregulation of microtubules is selected from the group consisting of a neuronal disease, such as Alzheimer disease or Schizophrenia, a cardiac disease, and a spinal injury.

The present invention also concerns a compound of formula (I) according to the invention, for use in a method of treatment of a cancer selected from the group consisting a cancer in need of stabilization of cell microtubules, preferably by a taxane, and a cancer induced by LKB1-deficient cells.

Preferably, the cancer treatable by a compound stabilizing cell microtubules is selected from the group consisting of breast cancer, ovarian cancer, liver cancer, lung cancer, pancreatic cancer and prostate cancer.

Preferably, the cancer induced by LKB1-deficient cells is selected from the group consisting of lung adenocarcinoma and uterus cancer, cervical cancer, breast cancer, intestinal cancer, testicular cancer, pancreatic cancer and skin cancer.

Advantageously, the compound of formula (I) according to the invention is used in a method of treatment of a cancer selected from the group consisting of breast cancer, ovarian cancer, lung cancer, liver cancer, uterus cancer and AIDS related Kaposi's sarcoma.

The present invention also concerns a compound of formula (I) according to the invention, for use in a method of treatment of a human or animal body, characterized in that said compound is co-administered with at least one compound stabilizing cell microtubules, preferably a human cell.

Preferably, the compound stabilizing cell microtubules is selected from the group consisting of taxanes, epothilones, TPI-287, carbazitaxel, zampanolide, dactylolide, discodermolide, taccalonolide, davunetide, eleutherobin, dictyostatin and sarcodictyins A and B, preferably taxanes.

Advantageously, the compound stabilizing cell microtubules is paclitaxel.

The present invention also concerns a compound of formula (I) according to the invention, for use in a method of treatment of a human or animal body, characterized in that said compound of formula (I) is administered to a patient having LKB1-deficient cells.

According to the invention, LKB1-deficient cells are cells that do not express the active liver kinase B1 (LKB1), because the STK11 gene, which encodes the LKB1, suffers from a germline mutation, or because they have inactivated LKB1 activity, through various mechanisms including mutations.

The invention will be better understood from reading the following non-limiting examples.

FIGURES

Figure 4:
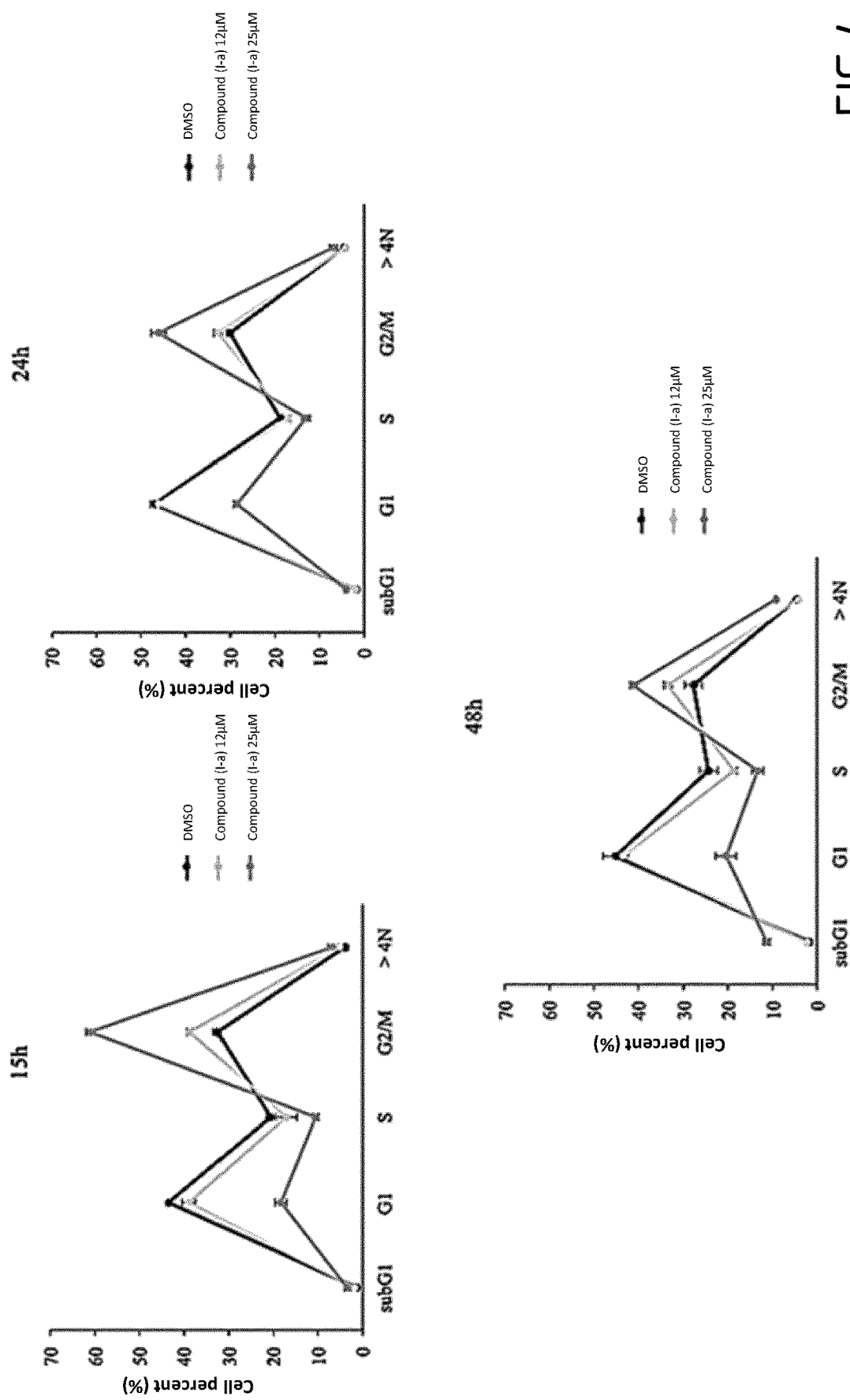

FIG. 4 shows the cell cycle distribution upon treatment of HeLa cells with compound (I-a) at a concentration of 12 µM or 25 µM, or with DMSO (control). The cell cycle was analyzed by flow cytometry. At steps subG1, G1 and S and after 24 hours, the curves corresponding to DMSO and compound (I-a) 12 µM are essentially superimposed.

Figure 5:
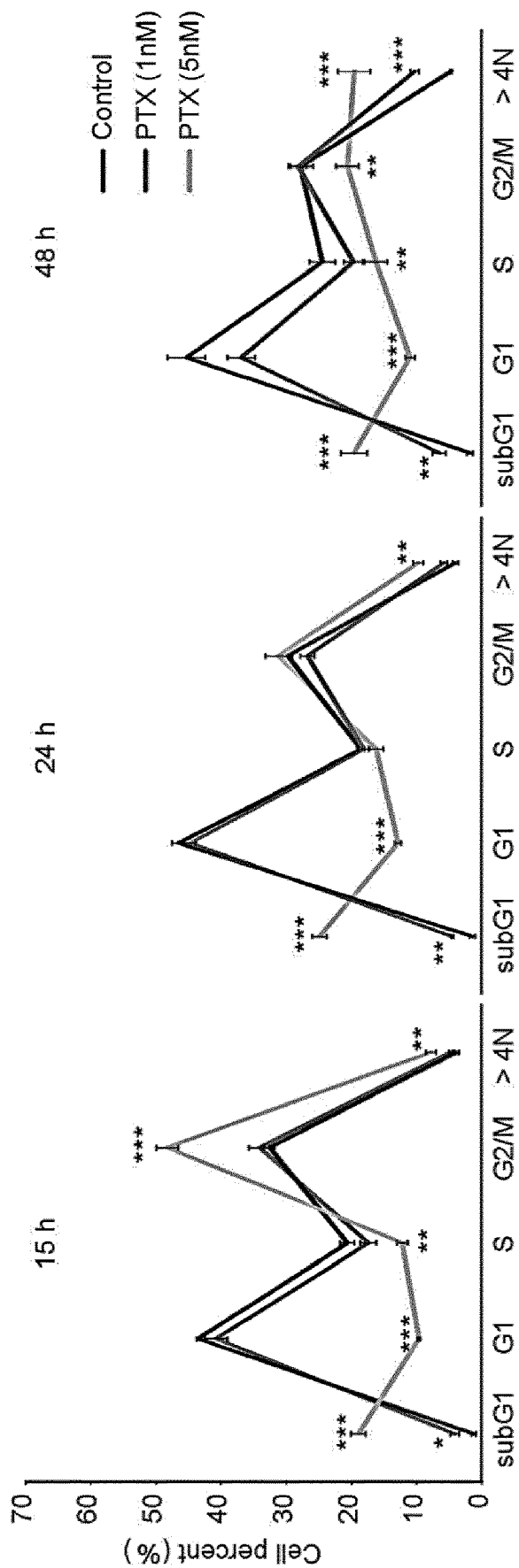

FIG. 5 shows the cell cycle distribution upon treatment of HeLa cells with paclitaxel at a concentration of 1 nM or 5 nM, or with DMSO (control). The cell cycle was analyzed by flow cytometry.

Figure 6:
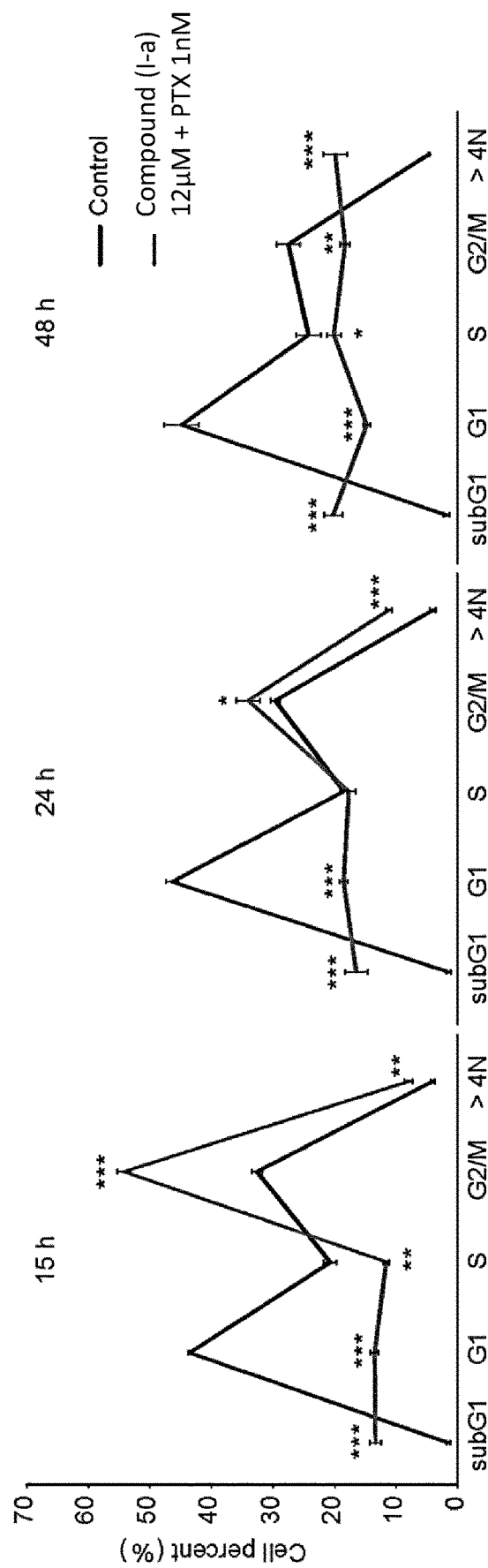

FIG. 6 shows the cell cycle distribution upon treatment of HeLa cells with a mixture of compound (I-a) (12 µM) and paclitaxel (1 nM), or with DMSO (control). The cell cycle was analyzed by flow cytometry.

Figure 7:
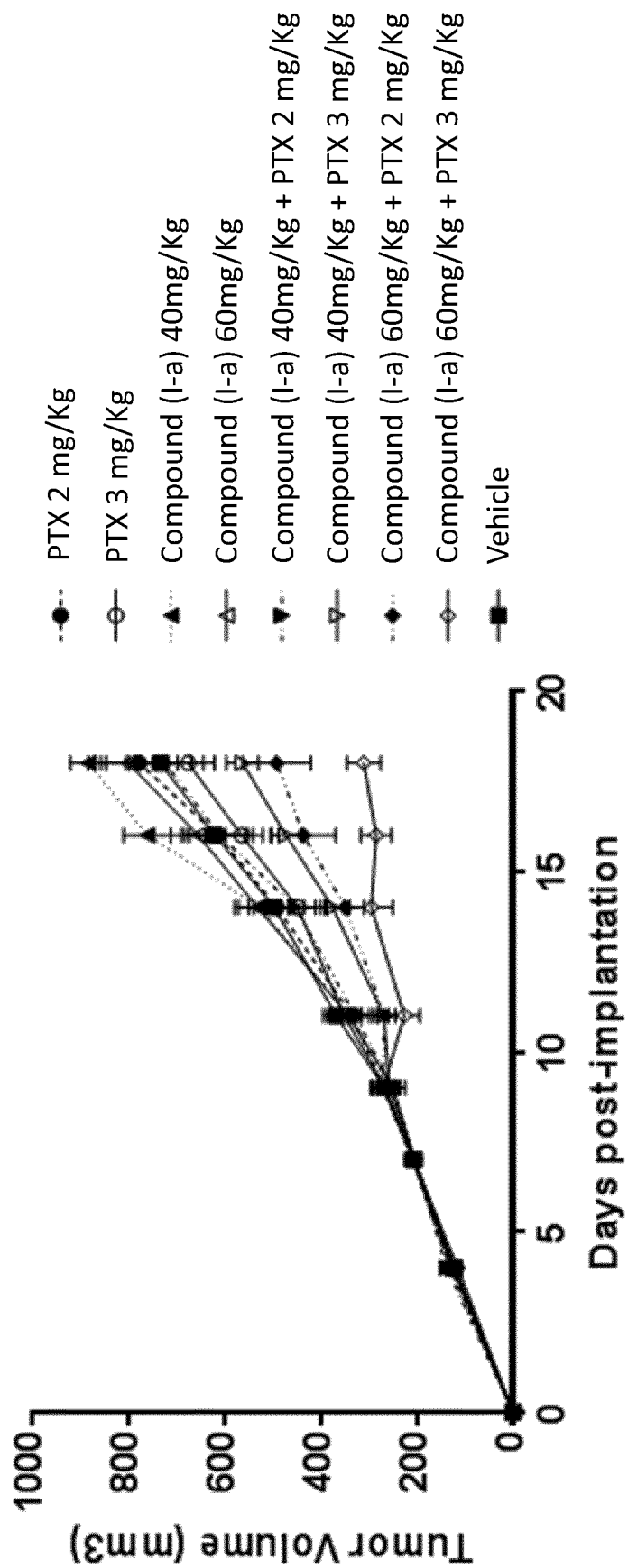

FIG. 7 is a graph representing the in-vivo evolution of the tumor size over time depending on the treatment received by the mice (paclitaxel alone, compound (I-a) alone or a combination of paclitaxel and compound (I-a)).

Figure 8:
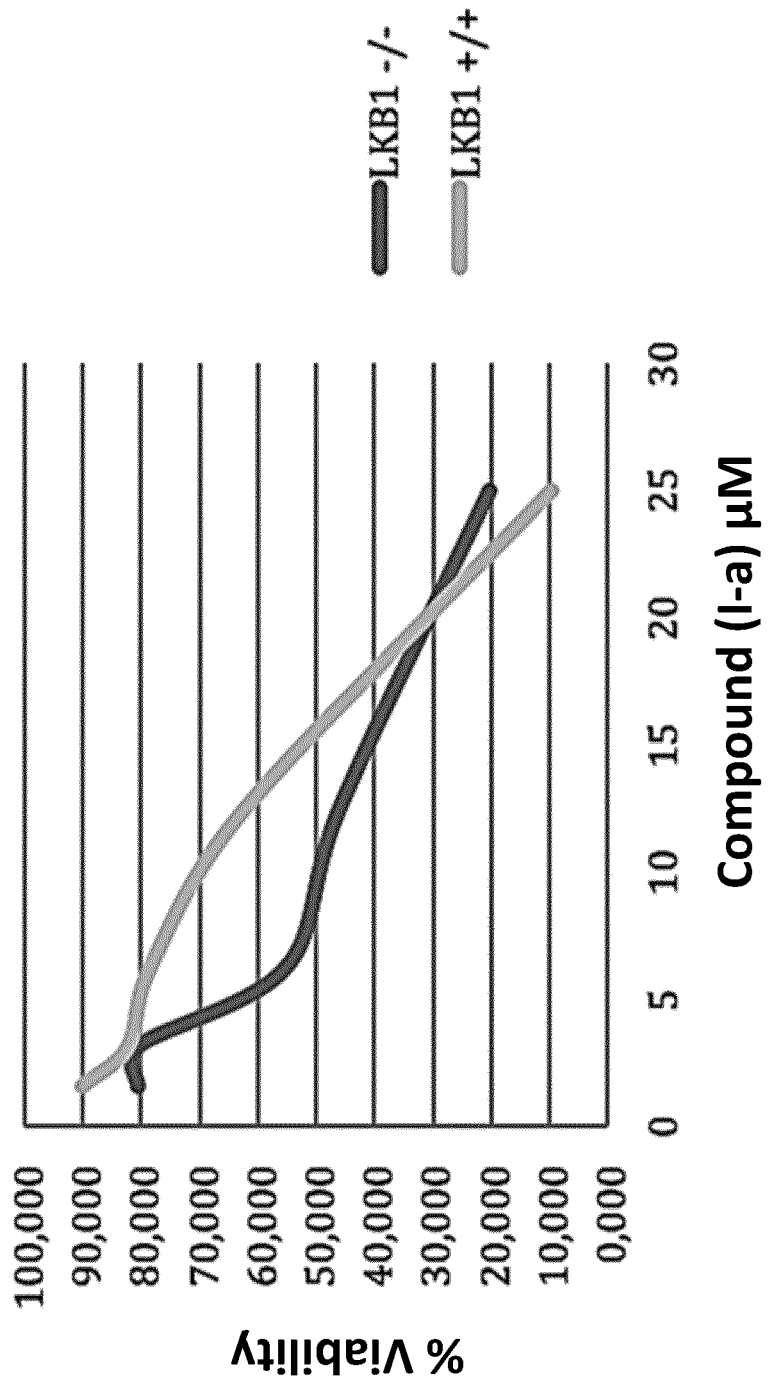

FIG. 8 is a graph representing the percentage of cell viability of LKB1-deficient cells or of cells in which LKB1 was reintroduced, depending on the concentration of compound (I-a).

Figure 9:
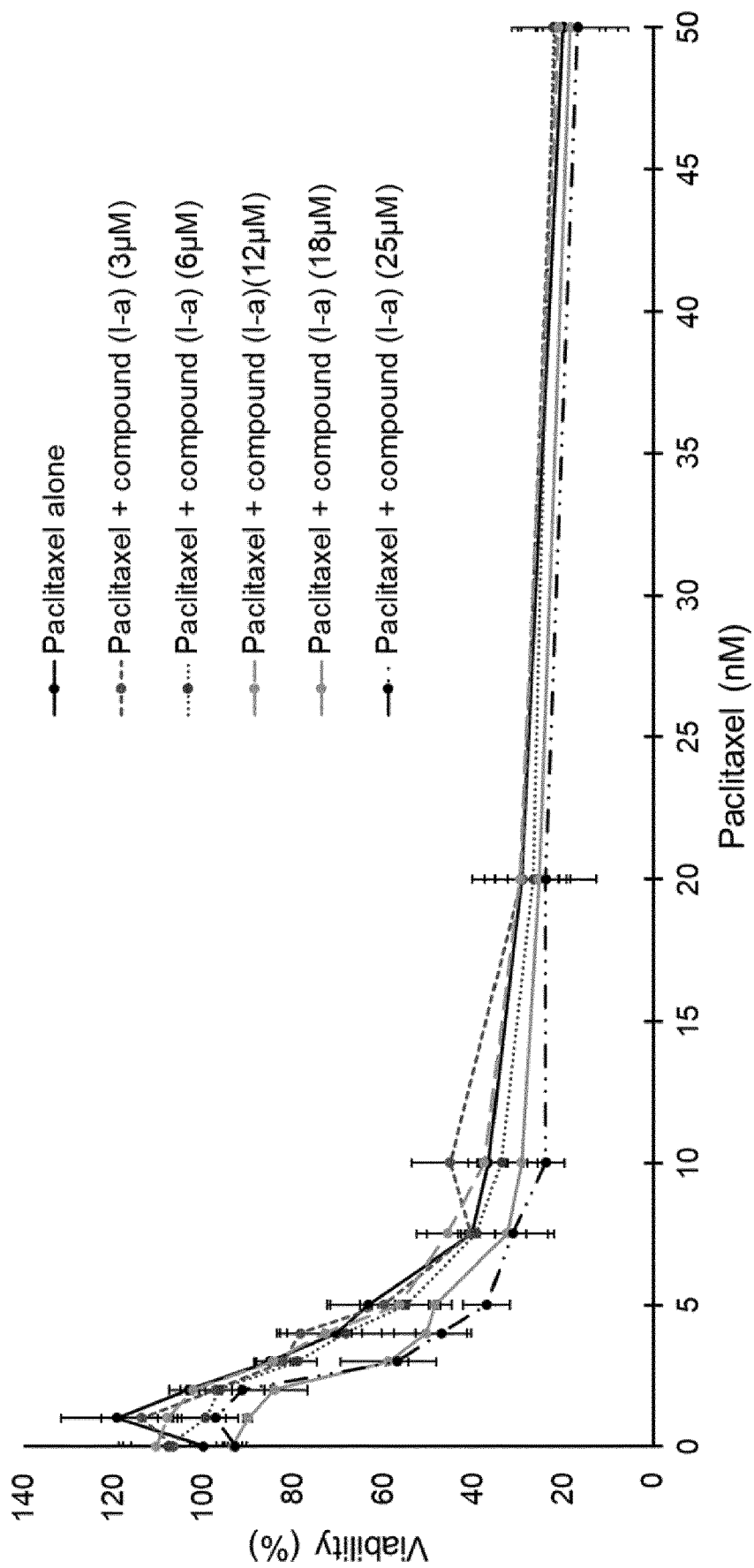

FIG. 9 is a graph representing the percentage of cell viability of RPE-1 cells incubated with compound (I-a) alone or with a combination of paclitaxel and compound (I-a).

EXAMPLES

Example 1: Synthesis of Compounds of Formula (I)

Compounds of formula (II) were synthesized according to the methods published in:

Tabka et al., European Journal of Medicinal Chemistry (1989), 24(6), 605-610,

Lancelot et al., Heterocyles (1990), 31(2),

Lancelot et al., Gazzetta chimica Italiana, 121, 1991,

Lancelot et al., (1986), 22$^{ème}$ Rencontres Internationales de chimie thérapeutique, Clermont-Ferrand, September 3-5, 124, Lancelot et al., (1989), 25$^{ème}$ Rencontres Internationales de chimie thérapeutique, Grenoble, July 2-5, Panno et al., Nuovi 1,4-Dimethil carbazoli: Sintesi, Reattivitàe valutazione Biologica. Tesi Di Dottorato d'Università Calabria: Università Della Calabria, 2011.

Compounds of formula (III-a) (CAS: 696-59-3), (III-c) (CAS: 50634-05-4) and (IV-b) (CAS-110-13-4) are commercially available.

Synthesis of Compounds (I-a), (I-d), (I-e), (I-f), (I-m), (I-n), (I-p), (I-q)

Compound of formula (III-a) (0.0033-0.0044 mol) was stirred 15 minutes at room temperature in 50 mL of acetic acid. Then, 1 equivalent of compound of formula (II-x) (x=a-i) was added. The mixture was heated at 80° C. for 1 h 30. After cooling, the solution was concentrated under reduced pressure. The residue was re-dissolved in 50 mL of a saturated solution of sodium hydrogenocarbonate, then extracted with 70 mL of ethyl acetate. The organic phase was washed with water, decanted, dried with magnesium sulfate and concentrated under reduced pressure. Compound of formula (I-x) (x=a, d, e, f, j, m, n, p, q) was obtained by crystallization in acetonitrile.

Synthesis of Compounds (I-c), (I-h), (I-k)

Compound of formula (III-c) (0.0041 mol) was stirred 15 minutes at room temperature in 50 mL of acetic acid. Then, 1 equivalent of compound of formula (II-x) (x=a, d, e) was added. The mixture was heated at 80° C. for 2 h. After cooling, the solution was concentrated under reduced pressure. The residue was re-dissolved in 50 mL of a saturated solution of sodium hydrogenocarbonate, then extracted with 70 mL of ethyl acetate. The organic phase was washed with water, decanted, dried with magnesium sulfate and evaporated. Compound of formula (I-x) (x=c, h, k) was obtained by crystallization in acetonitrile.

Synthesis of Compounds (I-b), (I-g), (I-o)

Compound of formula (II-x) (x=a, d, e, g) (0.0041-0.0049 mol) was heated at 80° C. for 2 hours in 50 mL of absolute ethanol in the presence of 1.2 equivalent of compound of formula (IV-b) and 0.3 mL of acetic acid. After cooling, the solution was concentrated under reduced pressure. The residue was re-dissolved in 40 mL of a saturated solution of sodium hydrogenocarbonate, then extracted with 60 mL of ethyl acetate. The organic phase was washed with water, decanted, dried with magnesium sulfate and concentrated under reduced pressure. Compound of formula (I-x) (x=b, g, j, o) was obtained by crystallization in acetonitrile.

Synthesis of Compound (I-s)

Compound of formula (I-c) (0.35 mmol) was stirred at 0° C. in 2 ml of dry methanol and 2 ml of dry tetrahydrofuran. 2 equivalents of sodium borohydrure were added. The mixture was stirred 2 h at room temperature. The solution was concentrated under reduced pressure. The residue was re-dissolved in 5 ml of ice water, then extracted two times with 5 ml of ethyl acetate. The organic phase was dried with magnesium sulfate and evaporated. Compound of formula (I-s) was obtained by purification by chromatography on silica gel (Diethyl) ether).

Compounds (I-a)-(I-q) and (I-s) were characterized by IR spectroscopy and/or NMR spectroscopy. Characteristics of each compound are gathered in the following table.

| Compound | $T_{fusion}$ (° C.) | IR (KBr) (cm$^{-1}$) | $^1$H NMR (DMSO-d$_6$) |
|---|---|---|---|
| (I-a) | 200 (acetonitrile) | 3380 (NH) | 2.54 (s, 3H, CH$_3$), 2.60 (s, 3H, CH$_3$), 6.28 (t, 2H, H-pyrroliques), 6.94 (t, 2H, H-pyrroliques), 7.23 (s, 1H, H$_2$), 7.50 (dd, 1H, H$_7$), 7.64 (d, 1H, H$_8$), 8.17 (d, 1H, H$_5$), 11.35 (s, 1H, NH). |
| (I-b) | 230 (ethanol) | 3390 (NH) | 1.88 (s, 6H, CH$_3$), 2.29 (s, 3H, CH$_3$), 2.60 (s, 3H, CH$_3$), 5.87 (s, 2H, H-pyrroliques), 7.11 (s, 1H, H$_2$), 7.48 (dd, 1H, H$_7$), 7.65 (d, 1H, H$_8$), 8.16 (d, 1H, H$_5$), 11.66 (s, 1H, NH). |
| (I-c) | 200 | 3320 (NH) 1661 (CO) | 2.55 (s, 3H, CH$_3$), 2.61 (s, 3H, CH$_3$), 6.73 (d, 1H, H-pyrrolique), 7.13 (s, 1H, H-pyrrolique), 7.30 (s, 1H, H$_2$), 7.50 (d, 1H, H$_7$), 7.63 (d, 1H, H$_8$), 7.86 (d, 1H, H-pyrrolique), 8.18 (d, 1H, H$_5$), 9.84 (s, 1H, CHO), 11.69 (s, 1H, NH). |
| (I-d) | 102 | 3374 (NH) | 2.59 (s, 3H, CH$_3$), 2.68 (s, 3H, CH$_3$), 6.26 (t, 2H, H-pyrroliques), 6.92 (t, 2H, H-pyrroliques), 7.25 (s, 1H, H$_2$), 7.27 (dd, 1H, H$_8$), 7.43 (t, 1H, H$_7$), 7.60 (dd, 1H, H$_6$), 11.79 (s, 1H, NH). |
| (I-e) | 189 | 3373 (NH) | 2.52 (s, 3H, CH$_3$), 2.58 (s, 3H, CH$_3$), 6.27 (t, 2H, H-pyrroliques), 6.93 (t, 2H, H-pyrroliques), 7.20 (s, 1H, H$_2$), 7.24 (dd, 1H, H$_6$), 7.60 (d, 1H, H$_5$), 8.16 (d, 1H, H$_8$), 11.60 (s, 1H, NH). |
| (I-f) | 195 (acetonitrile | 3380 (NH) | 2.48 (s, 3H, CH$_3$), 2.55 (s, 3H, CH$_3$), 6.23 (t, 2H, H-pyrroliques), 6,88 (t, 2H, H-pyrroliques), 7,17 (s, 1H, H$_2$), 7,55 (m, 2H, H7-H8), 8.24 (s, 1H, H$_5$), 11.59 (s, 1H, NH). |
| (I-g) | 216 (acetonitrile) | 3386 (NH) | 1.89 (s, 6H, CH$_3$), 2.30 (s, 3H, CH$_3$), 2.61 (s, 3H, CH$_3$), 5.87 (s, 2H, H-pyrroliques), 7.12 (s, 1H, H$_2$), 7.61 (m, 2H, H$_7$-H$_8$), 8.29 (s, 1H, H$_5$), 11.69 (s, 1H, NH). |
| (I-h) | 224 | 3285 (NH) 1654 (CO) | 2.57 (s, 3H, CH$_3$), 2.61 (s, 3H, CH$_3$), 6.72 (dd, 1H, H-pyrrolique), 7.14 (dd, 1H, H-pyrrolique), 7.31 (s, 1H, H$_2$), 7.59-7.65 (m, 2H, H$_7$-H$_8$), 7.87 (t, 1H, H-pyrrolique), 8.32 (d, 1H, H$_5$), 9.84 (s, 1H, CHO), 11.74 (s, 1H, NH). |
| (I-i) | 110 (hexane-diethyl ether) | 3400 (NH) | 2.40, 2,50 (s, 6H, CH$_3$), 6.20 (t, 2H, H-pyrroliques), 6.80 (t, 2H, H-pyrroliques), 7.20 (s, 1H, H$_2$), 7.35, 7.45 (m, 2H, H$_7$-H$_8$), 7.85 (q, 1H, H$_5$), 11.35 (s, 1H, NH). |
| (I-j) | 226 (acetonitrile) | 3389 (NH) | 1.88 (s, 6H, CH$_3$), 2.28 (s, 3H, CH$_3$), 2.55 (s, 3H, CH$_3$), 5.86 (s, 2H, H-pyrroliques), 7.08 (s, 1H, H$_2$), 7.34 (m, 1H, H$_7$), 7.61 (m, 1H, H$_8$), 7.91 (m, 1H, H$_5$), 11.51 (s, 1H, NH). |
| (I-k) | 222 | 3326 (NH) 1660 (CO) | 2.55 (s, 3H, CH$_3$), 2.60 (s, 3H, CH$_3$), 6.71 (m, 1H, H-pyrrolique), 7.13 (m, 1H, H-pyrrolique), 7.27 (s, 1H, H$_2$), 7.35 (td, 1H, H$_7$), 7.60 (dd, 1H, H$_8$), 7.85 (m, 1H, H-pyrrolique), 7.96 (dd, 1H, H$_5$), 9.83 (s, 1H, CHO), 11.59 (s, 1H, NH). |
| (I-m) | 179 (acetonitrile) | 3397 (NH) 3216 (OH) | 2.51 (s, 3H, CH$_3$), 2.56 (s, 3H, CH$_3$), 6.27 (t, 2H, H-pyrroliques), 6.93 (t, 2H, H-pyrroliques), 6.99 (dd, 1H, H$_7$), 7.12 (s, 1H, H$_2$), 7.43 (d, 1H, H$_8$), 7.57 (d, 1H, H$_5$), 9.00 (s, 1H, OH), 11.08 (s, 1H, NH). |
| (I-n) | 142 (diethyl ether) | 3380 (NH) 1732 (CO) | 1.35 (t, 3H, CH$_3$), 2.52 (s, 3H, CH$_3$), 2.60 (s, 3H, CH$_3$), 4.30 (q, 2H, CH$_2$), 6.27 (t, 2H, H-pyrroliques), 6.93 (t, 2H, H-pyrroliques), 7.21 (s, 1H, H$_2$), 7.33 (dd, 1H, H$_7$), 7.62 (d, 1H, H$_8$), 8.01 (d, 1H, H$_5$), 11.56 (s, 1H, NH). |
| (I-o) | 195 (acetonitrile) | 3398 (NH) 1742 (CO) | 1.34 (t, 3H, CH$_3$), 1.88 (s, 6H, CH$_3$), 2.27 (s, 3H, CH$_3$), 2.60 (s, 3H, CH$_3$), 4.30 (q, 2H, CH$_2$), 5.85 (s, 2H, H-pyrroliques), 7.08 (s, 1H, H$_2$), 7.33 (dd, 1H, H$_7$), 7.63 (d, 1H, H$_8$), 7.98 (d, 1H, H$_5$), 11.58 (s, 1H, NH). |
| (I-p) | 220 (ethanol) | 3330 (NH), 1685 (CO) | 2.46 (s, 3H, CH$_3$), 2.52 (s, 3H, CH$_3$), 3.95 (s, 3H, CH$_3$), 6.20 (t, 2H, H-pyrroliques), 6.82 (t, 2H, H-pyrroliques), 7.20 (s, 1H, H$_2$), 7.52 (d, 1H, H$_5$), 7.82 (dd, 1H, H$_7$), 8.70 (d, 1H, H$_8$), 11.40 (s, 1H, NH). |
| (I-q) | 169 | 3448 (NH), | 1.38 (t, 3H, CH$_3$), 2.54 (s, 3H, CH$_3$), 2.65 (s, 3H, CH$_3$), 3.10 (q, 2H, CH$_2$), 6.27 (t, 2H, H-pyrroliques), 6.93 (t, 2H, H-pyrroliques), 7.16 (s, 1H, H$_2$), 7.19 (dd, 1H, H$_6$), 7.30 (d, 1H, H$_5$), 8.02 (d, 1H, H$_7$), 11.58 (s, 1H, NH). |

| Compound | $T_{fusion}$ (° C.) | IR (KBr) (cm$^{-1}$) | $^1$H NMR (DMSO-d$_6$) |
|---|---|---|---|
| (I-s) | 142 | 3329 (NH), 3513 (OH) | 2.55 (s, 3H, CH$_3$), 2.58 (s, 3H, CH$_3$), 4.67 (d, 2H, CH$_2$), 6.36 (m, 1H, H-pyrrolique), 6.78 (t, 1H, H-pyrrolique ), 6.83 (t, 1H, H-pyrrolique), 7.18 (s, 1H, H$_2$), 7.42 (m, 2H, H$_7$ and H$_8$) 8.15 (s, 2H, H$_5$ and NH) |

Example 2: Assessment of the Cytotoxicity of Paclitaxel (PTX) in Combination with Compound of Formula (I)

2.1. Cytotoxicity on HeLa Cells

Cell viability was analyzed using the colorimetric Prestoblue assay (Invitrogen, #A13262). Cells were seeded in 96 well microplates (Greiner, #655077) at a density of 2,500 cells per well and allowed to adhere for 24 h before being treated for 72 h with either DMSO (0.1% final concentration) or drugs at indicated concentrations. After the 72 h treatment, 10 µL A Prestoblue was added to each well and cells were incubated for another 45 min. The absorbance of each well was measured using FLUOstar Optima microplate reader (Excitation, 544 nm; Emission, 580 nm).

First, the cytotoxicity on HeLa cells of compounds (I-a), (I-c) (I-f), (I-h), (I-e), (I-m), (I-n) and (I-s) was assessed with the above described "prestoblue" assay.

Compound (I-a) was found to be slightly cytotoxic, with a GI$_{50}$ (50% of growth inhibition) value of 19.4 OA to 21.8 µM.

Compounds (I-f) and (I-e) were also found to be slightly toxic, with GI$_{50}$ values of 16.2 µM and 14.8 µM, respectively. Compound (I-h) has a GI$_{50}$ value of 1.06 µM. Compounds (I-c) and (I-s) have both a GI$_{50}$ value of 2 µM.

Then, HeLa cells were treated during 72 hours with different concentrations of a mixture of paclitaxel (0.05, 0.1, 0.25, 0.5, 1, 2.5, 5 nM) and compounds (I-a), (I-f), (I-h), (I-e), (I-m), (I-n), (I-c) and (I-s).

The following results were obtained:

| | Concentration of compound (I-a) added to paclitaxel | | | |
|---|---|---|---|---|
| | 0 µM | 3 µM | 6 µM | 12 µM |
| GI$_{50}$ of Paclitaxel | 1.5 nM | 1.36 nM | 1.2 nM | 0.68 nM |

| | Concentration of compound (I-f) added to paclitaxel | | | |
|---|---|---|---|---|
| | 0 µM | 1.5 µM | 3 µM | 6 µM |
| GI$_{50}$ of Paclitaxel | 1.5 nM | 1.36 nM | 1.25 nM | 0.88 nM |

| | Concentration of compound (I-h) added to paclitaxel | | | |
|---|---|---|---|---|
| | 0 µM | 0.1 µM | 0.2 µM | 0.4 µM |
| GI$_{50}$ of Paclitaxel | 1.5 nM | 1.25 nM | 1.07 nM | 0.79 nM |

| | Concentration of compound (I-e) added to paclitaxel | | | |
|---|---|---|---|---|
| | 0 µM | 0.8 µM | 1.5 µM | 3 µM |
| GI$_{50}$ of Paclitaxel | 1.5 nM | 1.36 nM | 1.25 nM | 1.2 nM |

| | Concentration of compound (I-m) added to paclitaxel | | | |
|---|---|---|---|---|
| | 0 µM | 3 µM | 6 µM | 12 µM |
| GI$_{50}$ of Paclitaxel | 1.5 nM | 1.5 nM | 1.5 nM | 1.25 nM |

| | Concentration of compound (I-n) added to paclitaxel | | | |
|---|---|---|---|---|
| | 0 µM | 3 µM | 6 µM | 12 µM |
| GI$_{50}$ of Paclitaxel | 1.5 nM | 1.5 nM | 1.5 nM | 1.25 nM |

| | Concentration of compound (I-c) added to paclitaxel | |
|---|---|---|
| | 0 µM | 1.2 µM |
| GI$_{50}$ of Paclitaxel | 1.5 nM | 0.75 nM |

| | Concentration of compound (I-s) added to paclitaxel | |
|---|---|---|
| | 0 µM | 1.2 µM |
| GI$_{50}$ of Paclitaxel | 1.5 nM | 0.75 nM |

It can be observed that the GI$_{50}$ of paclitaxel is decreasing with the increase in compound (I-a) concentration.

At a concentration of 12 µM of compound (I-a) (concentration where compound (I-a) is not cytotoxic on its own), the GI$_{50}$ of paclitaxel is decreased by a factor 2.2 compared to the GI$_{50}$ of paclitaxel alone (1.5 nM vs. 0.68 nM).

Similar results are observed when combining compound (l-f), (l-h), (I-c) and (I-s) with paclitaxel, and in a lower extent when combining compound (I-e), (I-m) or (I-n) with paclitaxel.

These results highlight the synergistic effect of administering compounds of formula (I) in combination with paclitaxel.

2.2. Effect on Apoptosis

Apoptosis assay was performed with FITC Annexin V Apoptosis Detection Kit I (BD Biosciences, #556547) using flow cytometry and analyzed by FCS express software.

| Drug | DMSO | Paclitaxel (1 nM) | Compound (I-a) (12 µM) | Paclitaxel (1 nM) + Compound (I-a) (12 µM) | Compound (I-a) (25 µM) | Paclitaxel (1 nM) + Compound (I-a) (25 µM) |
|---|---|---|---|---|---|---|
| % of apoptosis | 14.21 ± 1.8 | 13.00 ± 0.48 | 13.13 ± 0.89 | 34.91 ± 2.73 | 29.23 ± 2.03 | 63.18 ± 3.05 |

No additional apoptosis was detected when compound (I-a) was applied for 48 hours at a concentration of 12 µM, when compared to DMSO, whereas at 25 µM, it induced cell death through apoptosis. These results indicate that compound (I-a) is moderately toxic.

When combined with paclitaxel, compound (I-a) also shows a synergistic effect on cell apoptosis.

2.3. Cytotoxicity on Murin Cancer Cells

Cell viability was analyzed using the colorimetric Prestoblue assay (Invitrogen, #A13262). Cells were seeded in 96 well microplates (Greiner, #655077) at a density of 2,500 cells per well and allowed to adhere for 24 h before being treated for 72 h with either DMSO (0.1% final concentration) or drugs at indicated concentrations. After the 72 h treatment, 10 µL Prestoblue was added to each well and cells were incubated for another 45 min. The absorbance of each well was measured using FLUOstar Optima microplate reader (Excitation, 544 nm; Emission, 580 nm).

Figure 1:
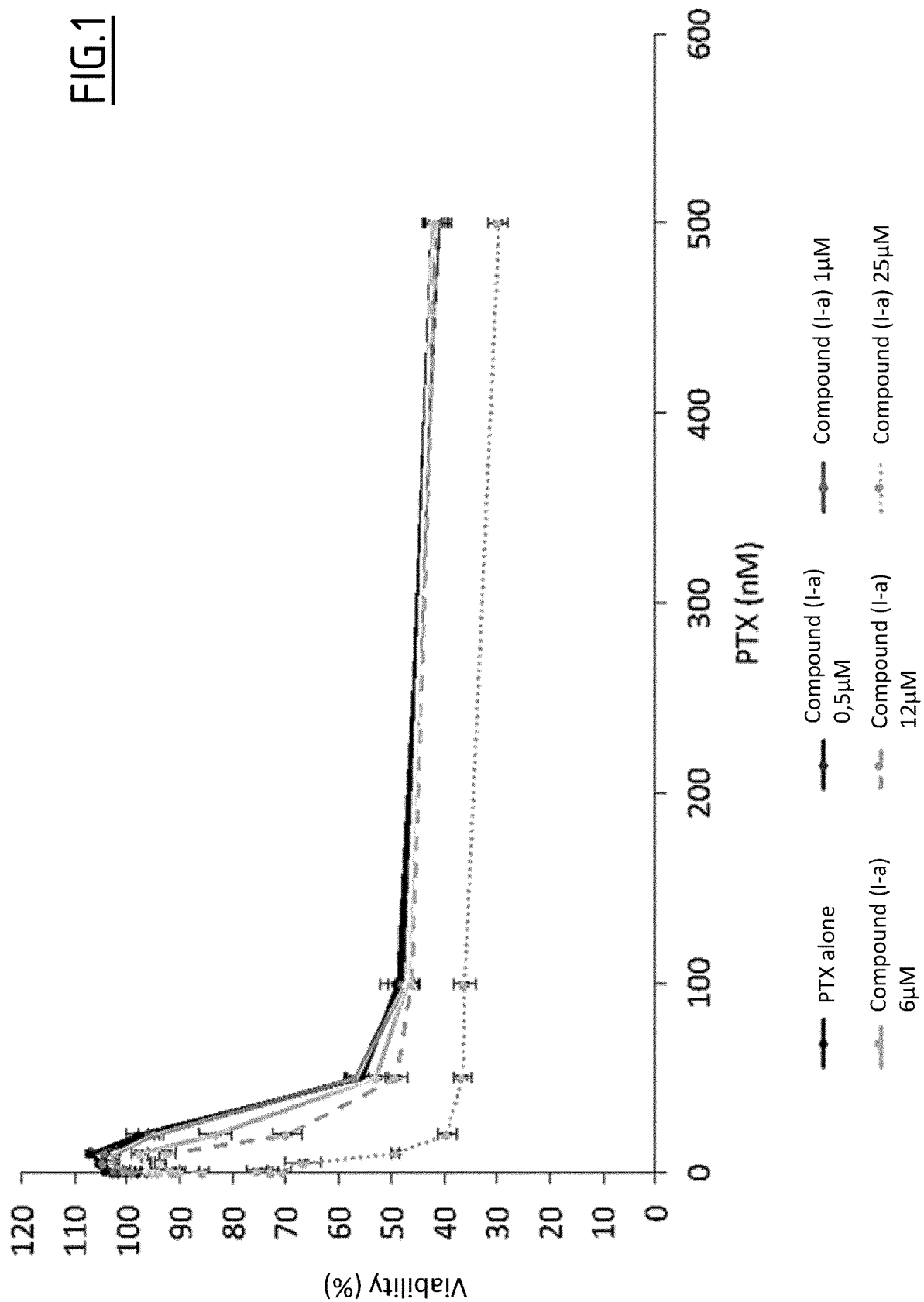
FIG. 1 shows the variation of HeLa cell viability as a function of paclitaxel (PTX) concentration, alone or in combination with compound (I-a) at various concentrations (0.5, 1, 6, 12 and 25 µM).

The synergistic effect of the combination of compound of formula (I-a) with paclitaxel is also observed on a mice breast cancer cell line (4T1 cells) (FIG. 1).

Example 3: Effect of a Compound of Formula (I) on Cell Cycle and Mitosis

The effect of a compound of formula (I) on cell cycle and mitosis of HeLa cells was analyzed by flow cytometry and immunofluorescence.

For flow cytometry analysis, Hela cells were treated with the indicated concentrations of compound (I-a) for 12 hours, 24 hours and 48 hours. Cells were then harvested and washed by centrifugation in PBS. Then, $10^5$ cells were fixed in 1 mL of 70% methanol at 4° C. overnight. Following two washes with PBS the cells were incubated with 50 µg·mL$^{-1}$ propidium iodide and 0.2 mg·mL$^{-1}$ RNase A/PBS for 30 min at 37° C. before analysis. The percentage of cells in the specific cell-cycle phases (G0, G1, S, G2, and M) was determined using an Accuri C6 flow cytometer (Becton Dickinson).

The results are expressed as the mean±SD of three separate experiments. The significance was determined by a Student's t-test (*p<0.05, p<0.01, *p<0.0001, compared with the control).

For immunofluorescence analysis, cells were grown for 48 hours on glass coverslips placed in 24-wells microplates. When cells reached 70% confluence the medium was replaced with a fresh one supplemented with compound (I-a). After a 5-hour exposure to compound (I-a), cells were fixed and permeabilized with −20° C. absolute methanol for 6 min. After washing and saturation with 3% BSA/PBS, cells were incubated for 45 min at room temperature (RT) with anti-alpha-tubulin antibody (1:4000). Cells were washed twice again and subsequently incubated with Alexa 488 conjugated anti-mouse antibody (1:1000) for 30 min at RT. DNA was stained with 20 µmol·L$^{-1}$ Hoechst 33342 and coverslips were mounted on microscopic slides with Mowiol 4-88 (Calbiochem, #475904). Images were captured with a Zeiss AxioimagerM2 microscope equipped with the acquisition software AxioVision and analyzed using the Fiji software.

Figure 2:
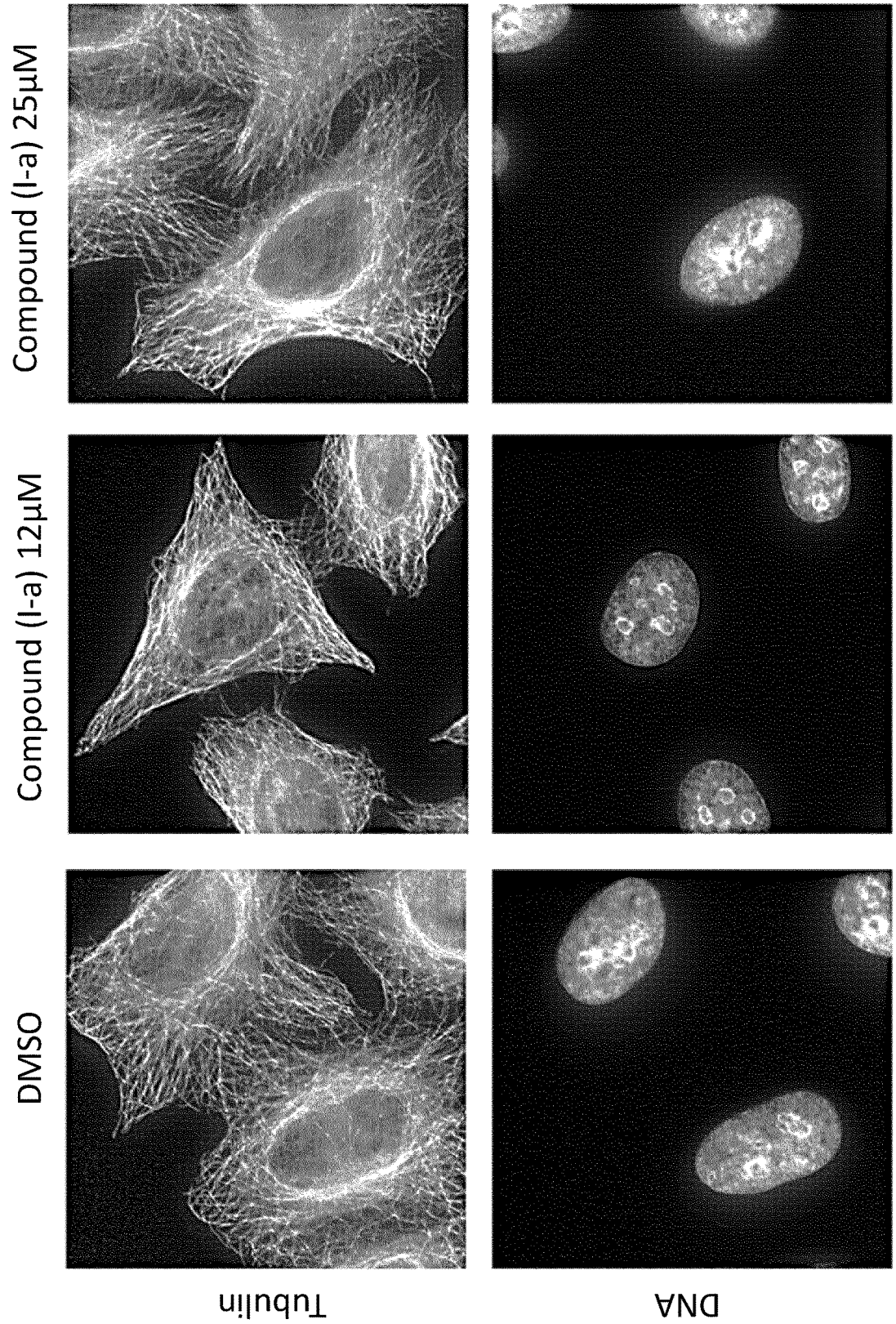
FIG. 2 shows images of cellular microtubules (top) and DNA (bottom) in cells treated with DMSO (control) or with 12 µM or 25 µM of compound (I-a).

The effect of compound (I-a) on cellular microtubules was determined. Compound (I-a) treatment (12-25 µM) does not visibly perturb microtubule network in the interphase cells (FIG. 2).

Figure 3:
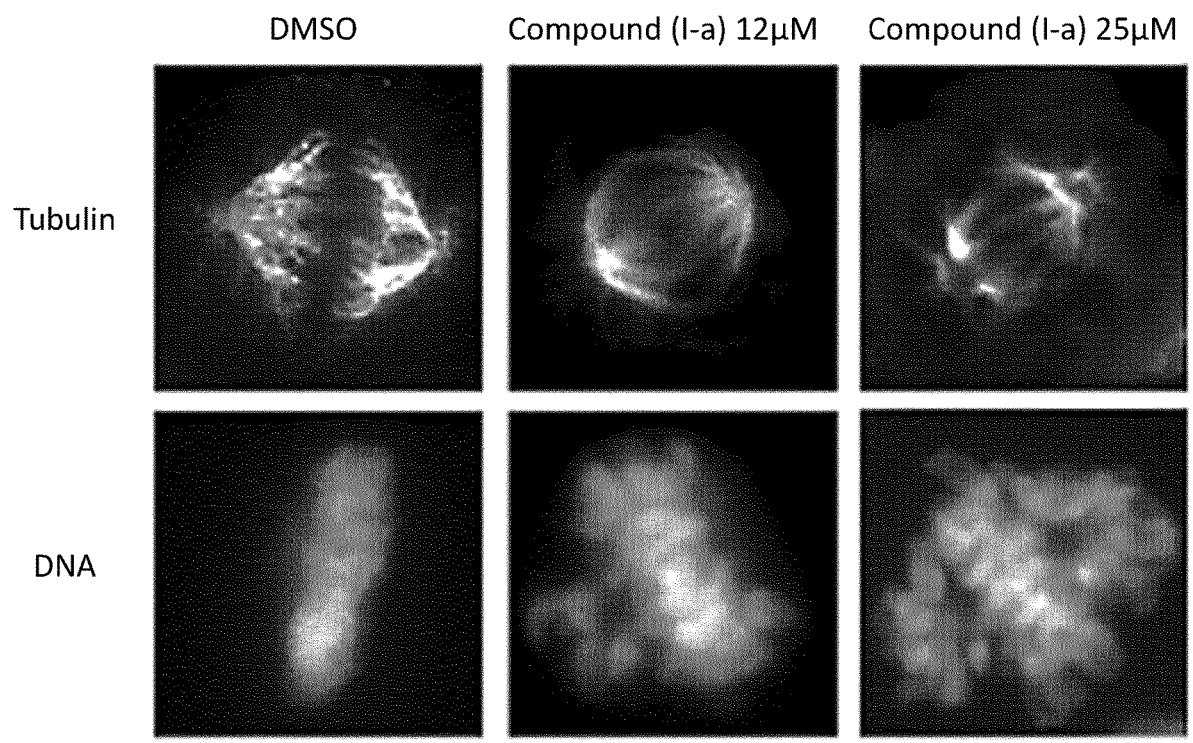
FIG. 3 shows images of chromosome congression in cells treated with DMSO (control) or with 12 µM or 25 µM of compound (I-a).

As shown on FIG. 3, chromosome congression defects were visible in several mitotic cells of the 12 µM treated cell population. The occurrence of such defects was increased at a higher dose (25 µM) of compound (I-a).

The effect of a high dose (25 µM) of compound (I-a) on microtubule dynamic instability parameters was measured using time-lapse fluorescence microscopy on GFP-EB3 transfected cells (Table 1).

TABLE 1

Analysis of the effect of Paclitaxel (1 nM) and compound (I-a) (25 µM) on microtubule dynamics

| Parameters | DMSO 0.25% | Compound (I-a) 25 µM |
|---|---|---|
| % time spent growing | 84.19 ± 0.20 | 60.40 ± 0.25*** |
| % time spent in pause | 15.81 ± 0.47 | 39.60 ± 0.31*** |
| Growth rate (µm/min ± SE) | 14.65 ± 0.10 | 10.20 ± 0.05*** |
| Catastrophe frequency (µm$^{-1}$ ± SE) | 0.23 ± 0.03 | 0.46 ± 0.05 *** |
| Catastrophe frequency (min$^{-1}$ ± SE) | 2.80 ± 0.61 | 2.74 ± 0.70 |

***p < 0.001, significantly different from control values (DMSO) using a Student's t test.

Compound (I-a) reduces the microtubule growth rate as well as the microtubule growth length, as indicated by the increase of the distance-based catastrophe frequency, and the increased time spent in pause, indicating that compound (I-a) at 25 µM suppresses microtubule dynamics.

Flow cytometry analysis indicated that a 12 µM concentration of compound (I-a) induces a significant delay in the completion of metaphase, because the cells are blocked in G2/M phase (FIG. 4). When compound (I-a) is applied at a concentration of 25 µM, the large majority of the cells is blocked in prometaphase.

Example 4: Effect of the Combination of a Compound of Formula (I) with Paclitaxel (PTX) on Cell Cycle and Mitosis Flow cytometry analysis was performed using HeLa cells. Hela cells were treated with the indicated concentrations of paclitaxel with or without compound (I-a) for 12 hours, 24 hours and 48 hours, then fixed with methanol, stained with propidium iodide and analyzed by flow cytometry. The results are expressed as the mean±SD of three separate experiments. The significance was determined by a Student's t-test (*p<0.05, p<0.01, *p<0.0001, compared with the control).

Flow cytometry analysis indicated that after 15 hours of treatment with 5 nM of paclitaxel, half of the cell population is blocked in G2/M phase and nearly 20% of the cells are already in apoptosis. Then, the proportion of cells in G2/M gradually decreases, in parallel with an increase in the number of cells in apoptosis (subG1) or plurinucleated. (FIG. 5).

As shown on FIG. 6, the combination of 1 nM paclitaxel (PTX) with 12 μM compound (I-a) induced a blockade of the cell cycle almost superimposable to the blockade observed when cells are treated with paclitaxel 5 nM. The similarity of the results obtained with the combination to those obtained with paclitaxel at 5 nM indicates that the overall effect of the combination results from an increase of paclitaxel effect by compound (I-a).

Example 5: Compound (I-a) and Paclitaxel (PTX) Act Synergistically on Tumor Growth In Vivo The effects on tumor growth of compound (I-a) and paclitaxel injected separately to the effect of a combined administration of compound (I-a) plus paclitaxel were compared in a tumor mouse model.

A first series of experiments (not shown) assessed that HeLa cell tumors were sensitive to therapeutic doses of paclitaxel. To that aim, mice bearing sizable tumors, formed of HeLa cells that have been xenografted, received intraveinous (i.v.) injections of paclitaxel (from 2 to 8 mg/Kg), every two days during 10 days. In the same experiment, the effect of compound (I-a) (from 15 to 60 mg/Kg, i.v.) injected with the same schedule was analyzed. The weight of paclitaxel or compound (I-a) treated animals and vehicle-treated animals were not significantly different. Moreover, the animals did not show any sign of discomfort, indicating a good tolerance to the treatments. Paclitaxel, when administered at 4 and 8 mg/Kg, induced an important reduction of tumor size. Compound (I-a) did not induce a significant effect on tumor size whatever the dose injected, although a tendency towards smaller tumors appears with increasing Compound (I-a) concentrations). The results confirmed the anti-tumor effect of high paclitaxel concentrations in this model. They also indicate that compound (I-a), when applied alone, has no significant anti-tumor activity, even at high concentrations.

A second experiment was conducted to study of the effect on tumor size of low (2 to 3 mg/Kg) paclitaxel doses in combination with different concentrations of compound (I-a).

Protocol for this combination study: 72 NMRI nude mice (5-week-old females) were injected subcutaneously with $10 \times 10^6$ exponentially dividing HeLa cells into the right flank. When tumors have reached a volume of about 200 mm 3 i.e. nine days after cell injection, mice were randomized in 9 groups of 8 mice each and drugs were injected intraveinously every two days. The first group received paclitaxel at 2 mg/kg, the second group received paclitaxel at 3 mg/Kg, the third group received compound (I-a) at 40 mg/Kg, the fourth group received compound (I-a) at 60 mg/Kg, the fifth group received a combination of compound (I-a) (40 mg/Kg) and paclitaxel (2 mg/Kg), the sixth group received a combination of compound (I-a) (40 mg/Kg) and paclitaxel (3 mg/Kg), the seventh group received a combination of compound (I-a) (60 mg/Kg) and paclitaxel (2 mg/Kg), the eight group received a combination of compound (I-a) (60 mg/Kg) and paclitaxel (3 mg/Kg) and the ninth group received the vehicle (14% DMSO, 14% Tween 80 and 72% PBS). Tumor growth was monitored three times per week with a sliding caliper.

No modification of body weight was observed throughout the study, suggesting that the combination is well tolerated. As shown in FIG. 7, while no effect is observed when each compound is administered separately, a significant effect on tumor size is observed with the combination of paclitaxel and compound (I-a). This anti-tumor effect varies dose-dependently, regarding compound (I-a) and paclitaxel concentrations. These results indicate that the observed synergy between paclitaxel and compound (I-a) in vitro also occurs in vivo, leading to a therapeutic efficacy.

Example 6: Assessment of the Effect of a Compound of Formula (I) on LKB1-Deficient Cells The synthetic lethality concept was applied to assess the selective toxicity of compounds of formula (I) on LKB1-deficient cells. This method consists in determining if the combination of the mutation conducting to the LKB1-deficiency and the action of compound of formula (I) causes lethality, whereas this mutation is not lethal in itself nor is the compound of formula (I) when applied alone.

The differential cytotoxicity of compounds (I) on LKB1-deficient cells was determined on MEF KO LKB1 cells (LKB1-deficient cells) or cells in which LKB1 was reintroduced. Cell viability analysis using MTT: the assay was performed in 96-well microplates. LKB1 KO MEF cells (LKB1−/−) and LKB1 rescued MEF cells (LKB1+/+) were seeded at 20,000 cells per well and allowed to grow for 24 hours. The culture medium was then replaced with a fresh medium containing compound (I-a) (0 to 25 μM), or DMSO (0.25%). Cells were allowed to grow for additional 48 hours. Then, 20 μL of 3-(4,5-dimethylthiazol-2-yl)-2,5-diphenyl-tetrazolium bromide (MTT) solution at 5 mg/mL was added to each well and incubated for 4 h at 37° C. The culture medium was discarded, and 100 μL of a solution DMSO: ethanol (1:1) was added into each well and mixed by gently shaking for 10 min. Absorbance was measured in a microplate reader at 570 nm.

The results obtained are presented in FIG. 8.

Example 7: Assessment of the Effect of a Compound of Formula (I) in Combination with Paclitaxel on the Viability of Non-Cancerous Cells RPE-1 cells were incubated for 72 hours with the indicated combinations of compound (I-a)/paclitaxel. The percentage of viable cells was calculated following a Prestoblue assay, as described above. Data are presented as mean±SEM of 3 independent experiments.

The results obtained are presented in FIG. 9.

It can be seen that compounds of formula (I) do not exhibit toxicity toward non-cancerous cells. (Note that the effect on cell viability of the different doses of compound (I-a) alone can be seen at the x-coordinate=0 of the graph of FIG. 9, corresponding to 0 nM of paclitaxel). GI50 for PTX (7 nM) was higher in this cell line than in HeLa cells. When used in combination with PTX, compound I-a was able to synergistically affect cell viability, at high dose (25 µM). These results indicate that compound (I-a) does not induce additional toxicity.

The invention claimed is:
1. A compound of formula (I)

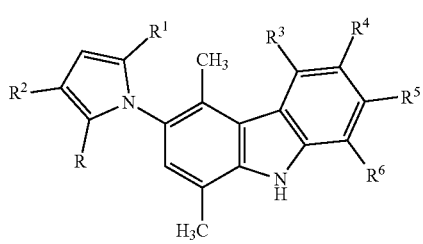

wherein R, $R^1$ and $R^2$ are independently selected form the group consisting of:
  a hydrogen atom,
  a halogen atom,
  an optionally substituted linear, cyclic or branched, saturated or unsaturated, alkyl group comprising from 1 to 10 carbon atoms,
  an acyl group comprising from 1 to 10 carbon atoms,
  a carboxyl group,
  an amido group comprising from 1 to 10 carbon atoms, and
    an imino group, optionally substituted by a linear, cyclic or branched, saturated or unsaturated alkyl group, and
wherein $R^3$, $R^4$, $R^5$ and $R^6$ are independently selected form the group consisting of:
  a hydrogen atom,
  a halogen atom,
  a hydroxyl group,
    an optionally substituted linear, cyclic or branched, saturated or unsaturated alkyl group comprising from 1 to 10 carbon atoms,
  an alkoxy group comprising from 1 to 10 carbon atoms,
  an acyl group comprising from 1 to 10 carbon atoms,
  a carbonate group from 1 to 10 carbon atoms,
  a carboxyl group, and
  a cyano group.

2. The compound according to claim 1, wherein R, $R^1$ and $R^2$ are independently selected from the group consisting of:
  a hydrogen atom,
  a halogen atom,
  an alkyl group of formula —$C_nH_{2n+1-x}X_x$, wherein X is selected from the group consisting of a hydrogen atom, a halogen atom, a hydroxyl group, n is an integer between 1 and 10 and x is the number of X present in the alkyl group,
  an acyl group of formula —$C(O)OR_a$, wherein $R_a$ is a linear and saturated alkyl group comprising from 1 to 9 carbon atoms,
  an acyl group of formula —$C(O)H$,
  a carboxyl group (—COOH),
  an amido group of formula —$C(O)NR_b$, wherein $R_b$ is a linear and saturated alkyl group comprising from 1 to 9 carbon atoms, and
  an imino group of formula —$C=N-R_c$, wherein $R_c$ is selected from the group consisting of a hydrogen atom or a linear, saturated alkyl group comprising from 1 to 10 carbon atoms, and a phenyl group, and wherein $R^3$, $R^4$, $R^5$ and $R^6$ are independently selected from the group consisting of:
  a hydrogen atom,
  a halogen atom,
  a hydroxyl group,
  a linear, saturated alkyl group of formula —$C_nH_{2n+1}$, wherein n is an integer between 1 and 10,
  an alkoxy group of formula —$OR_d$, wherein $R_d$ is a linear and saturated alkyl group comprising from 1 to 9 carbon atoms,
  an acyl group of formula —$C(O)OR_a$, wherein $R_a$ is a linear and saturated alkyl group comprising from 1 to 9 carbon atoms,
  an acyl group of formula —$C(O)R_e$, wherein $R_e$ is a hydrogen atom or a linear, cyclic or branched, saturated or unsaturated, optionally substituted alkyl group comprising from 1 to 10 carbon atoms,
  a carbonate group comprising from 1 to 10 carbon atoms,
  a carboxyl group (—COOH), and
  a cyano group (—CN).

3. The compound according to claim 1, wherein R and $R^1$ are independently selected from the group consisting of:
  a hydrogen atom,
  a halogen atom,
  a linear, saturated alkyl group comprising from 1 to 10 carbon atoms,
wherein $R^2$ is selected from the group consisting of:
  a hydrogen atom,
  a halogen atom,
  an alkyl group of formula —$C_nH_{2n+1-x}X_x$, wherein X is selected from the group consisting of a hydrogen atom, a halogen atom, a hydroxyl group, n is an integer between 1 and 10 and x is the number of X present in the alkyl group,
  an acyl group of formula —$C(O)OR_a$, wherein $R_a$ is a linear and saturated alkyl group comprising from 1 to 9 carbon atoms,
  an acyl group of formula —$C(O)H$,
  a carboxyl group (—COOH),
  an amido group of formula —$C(O)NR_b$, wherein $R_b$ is a linear and saturated alkyl group comprising from 1 to 9 carbon atoms, and
  an imino group of formula —$C=N-R_c$, wherein $R_c$ is selected from the group consisting of a hydrogen atom or a linear, saturated alkyl group comprising from 1 to 10 carbon atoms, and a phenyl group, wherein $R^3$, $R^5$ and $R^6$ are independently selected from the group consisting of:
  a hydrogen atom,
  a halogen atom,
  a linear, saturated alkyl group of formula —$C_nH_{2n+1}$, wherein n is an integer between 1 and 10, and
wherein $R^4$ is selected from the group consisting of:
  a hydrogen atom,
  a halogen atom,
  a hydroxyl group,
  a linear, saturated alkyl group of formula —$C_nH_{2n+1}$, wherein n is an integer between 1 and 10,
  an alkoxy group of formula —$OR_d$, wherein $R_d$ is a linear and saturated alkyl group comprising from 1 to 9 carbon atoms,
  an acyl group of formula —$C(O)OR_a$, wherein $R_a$ is a linear and saturated alkyl group comprising from 1 to 9 carbon atoms,
  an acyl group of formula —$C(O)R_e$, wherein $R_e$ is a hydrogen atom or a linear, cyclic or branched, saturated or unsaturated, optionally substituted alkyl group comprising from 1 to 10 carbon atoms, a carbonate group of formula —OC(O)OR$_f$, wherein R$_f$ is a linear and saturated alkyl group comprising from 1 to 9 carbon atoms, a carboxyl group (—COOH), and a cyano group (—CN).

4. The compound according to claim 1, wherein R and R$^1$ are independently selected from the group consisting of a hydrogen atom, a chloride atom and a methyl group, wherein R$^2$ is selected from the group consisting of a hydrogen atom, a methyl group, a —COH group, an alkyl group of formula —CH$_2$X, wherein X is selected from the group consisting of a chloride atom, a bromide atom, a iodine atom and a hydroxyl group, an acyl group of formula —C(O)OR$_a$, wherein R$_a$ is a methyl group or an ethyl group, an acyl group of formula —C(O)H, a carboxyl group (—COOH), an amido group of formula —C(O)NR$_b$, wherein R$_b$ is a methyl group or an ethyl group, and an imino group of formula —C=N—R$_c$, wherein R$_c$ is a phenyl group, wherein R$^3$, R$^5$ and R$^6$ are independently selected from the group consisting of a hydrogen atom, a chloride atom, a methyl group and an ethyl group, and wherein R$^4$ is selected from the group consisting of a hydrogen atom, a methyl group, a hydroxyl group, a chloride atom, a bromide atom, a fluoride atom, a iodine atom, an alkoxy group of formula —OR$_d$, wherein R$_d$ is a methyl group or an ethyl group, an acyl group of formula —C(O)OR$_a$, wherein R$_a$ is a methyl group or an ethyl group, an acyl group of formula —C(O)R$_e$, wherein R$_e$ is a methyl group, an ethyl group, a linear propyl group, a linear pentyl group, —CH$_2$CH$_2$-cyclopentyl group and a (para-methyl)phenyl group, a carbonate group of formula —OC(O)OR$_f$, wherein R$_f$ is a methyl group or an ethyl group, a carboxyl group (—COOH), and a cyano group (—CN).

5. The compound according to claim 1, wherein R and R$^1$ are independently selected from the group consisting of a hydrogen atom and a methyl group, wherein R$^2$ is selected from the group consisting of a hydrogen atom, a —COH group and a —CH$_2$OH group, wherein R$^3$, R$^5$ and R$^6$ are independently selected from the group consisting of a hydrogen atom, a chloride atom and an ethyl group, and wherein R$^4$ is selected from the group consisting of a hydrogen atom, a hydroxyle group, a chloride atom, a bromide atom, a fluoride atom, a carbonate group of formula —OC(O)OR$_f$, wherein R$_f$ is an ethyl group and an acyl group of formula —C(O)OR$_a$, wherein R$_a$ is a methyl group.

6. The compound according to claim 1, characterized in that at least three of the substituents selected from the group consisting of R$^3$, R$^4$, R$^5$ and R$^6$ are a hydrogen atom.

7. The compound according to claim 1, characterized in that said compound is selected from the group consisting of

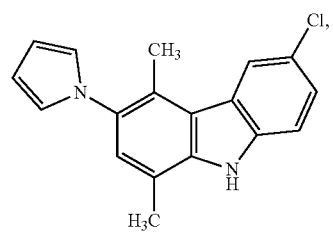

(I-a)

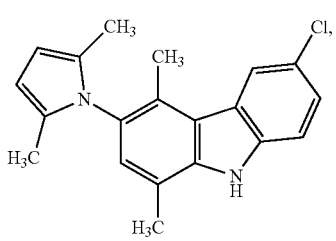

(I-b)

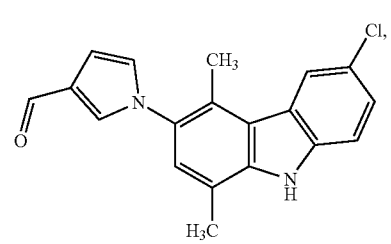

(I-c)

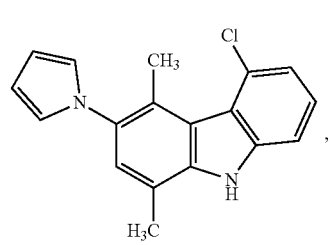

(I-d)

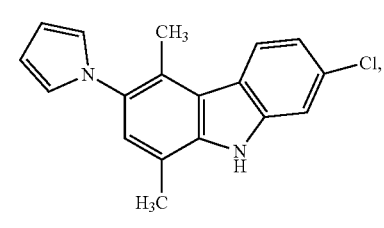

(I-e)

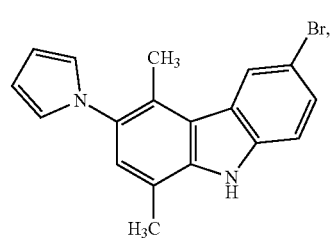

(I-f)

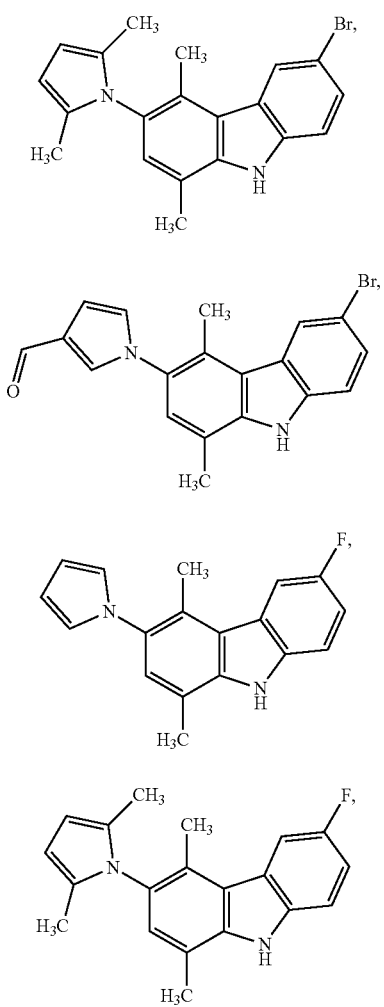
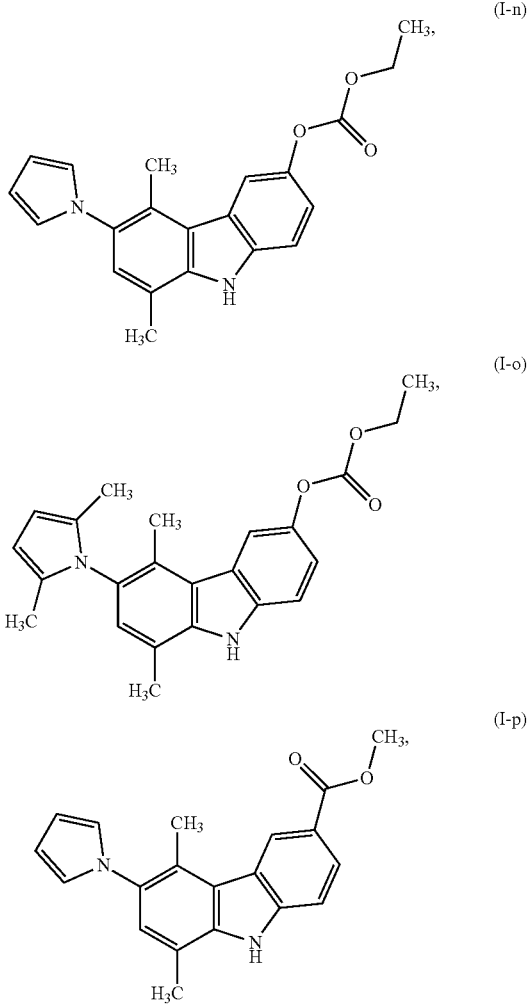
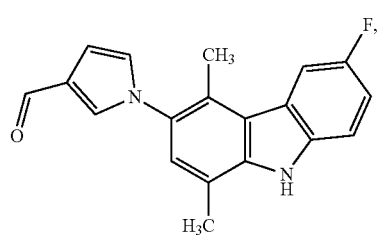
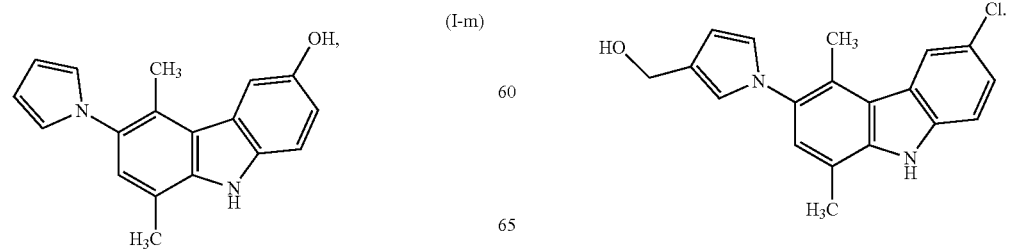

8. A method of preparation of a compound according to claim 1, comprising a step a) of contacting a compound of formula (II)

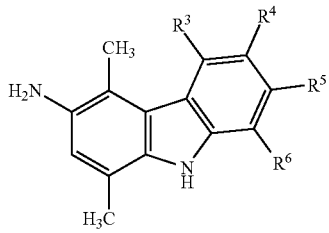
(II)

with a compound of formula (III)

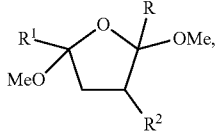
(III)

or a compound of formula (IV)

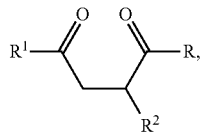
(IV)

in the presence of an acid, preferably of an organic acid, wherein R, $R^1$ and $R^2$ are independently selected from the group consisting of:
- a hydrogen atom,
- a halogen atom,
- a linear, cyclic or branched, saturated or unsaturated, optionally substituted alkyl group comprising from 1 to 10 carbon atoms,
- an acyl group comprising from 1 to 10 carbon atoms,
- a carboxyl group,
- an amido group comprising from 1 to 10 carbon atoms, and
- an imino group, optionally substituted by a linear, cyclic or branched, saturated or unsaturated alkyl group and wherein $R^3$, $R^4$, $R^5$ and $R^6$ are independently selected from the group consisting of:
- a hydrogen atom,
- a halogen atom,
- a hydroxyl group,
- a linear, cyclic or branched, saturated or unsaturated, optionally substituted alkyl group comprising from 1 to 10 carbon atoms,
- an alkoxy group comprising from 1 to 10 carbon atoms,
- an acyl group comprising from 1 to 10 carbon atoms,
- a carbonate group from 1 to 10 carbon atoms,
- a carboxyl group, and
- a cyano group.

9. A pharmaceutical composition, comprising at least one compound according to claim 1 and at least one pharmaceutically-acceptable excipient.

10. A method for treating a disease and/or a disorder selected from the group consisting of a cancer and a disorder involving a deregulation of microtubules comprising administering to a mammal in need thereof a therapeutically effective amount of compound according to claim 1.

11. A method for treating a cancer selected from the group consisting of a cancer in need of stabilization of cell microtubules, and a cancer induced by LKB1-deficient cells comprising administering to a mammal in need thereof a therapeutically effective amount of a compound according to claim 1.

12. A method for treating a cancer comprising administering to a mammal in need thereof a therapeutically effective amount of a compound according to claim 1 wherein said compound is co-administered with at least one compound that stabilizes cell microtubules.

13. The method according to claim 12, wherein said at least one compound that stabilizes cell microtubules is selected from the group consisting of taxanes, epothilones, TPI-287, carbazitaxel, zampanolide, dactylolide, discodermolide, taccalonolide, davunetide, eleutherobin, dictyostatin and sarcodictyins A and B.

14. The method according to claim 12, wherein said at least one compound that stabilizes cell microtubules is paclitaxel.

15. A method of treating a human or animal patient having LKB1-deficient cells, comprising administering to the human or animal patient a therapeutically effective amount of a compound of claim 1.

* * * * *